US012485243B2

(12) United States Patent
Samuel et al.

(10) Patent No.: US 12,485,243 B2
(45) Date of Patent: Dec. 2, 2025

(54) SANITARY EXTUBATION COVER AND METHOD FOR ITS USE

(71) Applicant: RTM Medical LLC, Huntingdon Valley, PA (US)

(72) Inventors: Rick Samuel, Huntingdon Valley, PA (US); Todd Burlingame, Jenkintown, PA (US); David Nichols, Dallas Forth Worth, TX (US); Doug Crow, Brownsboro, TX (US); William Douglas, Jacksonville, TX (US)

(73) Assignee: RTM Medical LLC, Huntingdon Valley, PA (US)

( * ) Notice: Subject to any disclaimer, the term of this patent is extended or adjusted under 35 U.S.C. 154(b) by 556 days.

(21) Appl. No.: 17/140,040

(22) Filed: Jan. 1, 2021

(65) Prior Publication Data

US 2022/0193357 A1 Jun. 23, 2022

Related U.S. Application Data

(60) Provisional application No. 63/128,206, filed on Dec. 21, 2020.

(51) Int. Cl.
*A61M 16/06* (2006.01)
*A61M 16/04* (2006.01)

(52) U.S. Cl.
CPC .... *A61M 16/0622* (2014.02); *A61M 16/0402* (2014.02); *A61M 2205/02* (2013.01)

(58) Field of Classification Search
CPC ......... A62B 18/02; A62B 18/025; A62B 7/12; A61M 16/06; A61M 16/0622; A61M 16/0875; A61M 39/08
See application file for complete search history.

(56) References Cited

U.S. PATENT DOCUMENTS

| | | | | |
|---|---|---|---|---|
| 1,120,549 A | | 12/1914 | Scheilberg | |
| 2,164,330 A | * | 7/1939 | Katz | A62B 18/02 128/201.19 |

(Continued)

FOREIGN PATENT DOCUMENTS

| | | | | |
|---|---|---|---|---|
| KR | 20190034924 A | * | 4/2019 | A61M 39/10 |
| WO | WO-2019014344 A1 | * | 1/2019 | A61M 25/0017 |
| WO | WO-2021191884 A1 | * | 9/2021 | A41D 13/1107 |

OTHER PUBLICATIONS

PCT/US2021/035800 (counterpart to U.S. Appl. No. 16/894,703) U.S. International /Search Report and the Written Opinion of the International Searching Authority, International Preliminary Report on Patentability, and related documents.

*Primary Examiner* — Kathryn E Ditmer
(74) *Attorney, Agent, or Firm* — Muskin and Farmer LLC

(57) ABSTRACT

A sanitary extubation cover used to cover an endotracheal tube and a patient's face in order to accommodate sanitary extubation. The sanitary extubation cover includes a mask and a cover which covers the endotracheal tube. If the patient coughs, the cough would be directed into the mask and the endotracheal tube (which is covered by the cover) but contaminants from the cough would be suppressed from spreading into the open air. The mask can have an air cushion at the bottom of the mask in order to securely press against the patient's face. The mask can also have a solid silicone base at the bottom of the mask in order to securely press against the patient's face.

2 Claims, 44 Drawing Sheets

(56) References Cited

U.S. PATENT DOCUMENTS

| | | | | | | |
|---|---|---|---|---|---|---|
| 2,428,451 | A | * | 10/1947 | Emerson | A61M 16/0075 | 137/512.1 |
| 3,556,097 | A | | 1/1971 | Wallace | | |
| 3,902,500 | A | * | 9/1975 | Dryden | A61M 16/0463 | 128/207.14 |
| 3,905,361 | A | | 9/1975 | Hewson | | |
| 4,449,526 | A | | 5/1984 | Elam | | |
| 4,502,480 | A | * | 3/1985 | Yamamoto | A42B 3/288 | 128/201.15 |
| 4,537,189 | A | * | 8/1985 | Vicenzi | A62B 9/00 | 128/202.13 |
| 4,579,108 | A | | 4/1986 | Bauman | | |
| 4,669,462 | A | * | 6/1987 | Marshall | A62B 7/02 | 128/202.13 |
| 4,723,912 | A | * | 2/1988 | Nieusma | A61C 1/16 | 433/116 |
| 4,744,358 | A | | 5/1988 | McGinnis | | |
| 4,772,275 | A | * | 9/1988 | Erlich | A61M 25/0111 | 604/523 |
| 4,878,486 | A | | 11/1989 | Slater | | |
| 4,951,661 | A | * | 8/1990 | Sladek | A61M 16/0808 | 128/205.24 |
| 5,078,131 | A | | 1/1992 | Foley | | |
| 5,242,398 | A | | 9/1993 | Knoll | | |
| 5,336,193 | A | | 8/1994 | Rom | | |
| 5,343,849 | A | | 9/1994 | Steer | | |
| 5,345,931 | A | | 9/1994 | Battaglia | | |
| 5,357,945 | A | * | 10/1994 | Messina | A61M 16/0875 | 128/203.29 |
| 5,515,846 | A | * | 5/1996 | Drews | A62B 18/02 | 128/206.28 |
| 5,582,599 | A | | 12/1996 | Daneshvar | | |
| 5,660,174 | A | | 8/1997 | Jacobelli | | |
| 5,746,199 | A | * | 5/1998 | Bayron | A61M 16/20 | 128/205.24 |
| 5,810,001 | A | * | 9/1998 | Genga | A61M 16/183 | 128/203.12 |
| 7,159,589 | B2 | | 1/2007 | Brain | | |
| 8,726,903 | B2 | | 5/2014 | Levine | | |
| 8,960,195 | B2 | | 2/2015 | Lehman | | |
| 9,694,150 | B2 | | 7/2017 | Brain | | |
| 10,016,575 | B2 | | 7/2018 | Vazales | | |
| 10,646,676 | B1 | | 5/2020 | Matich | | |
| 10,905,905 | B1 | * | 2/2021 | Dettore | A62B 23/025 | |
| 11,040,161 | B1 | | 6/2021 | Bui | | |
| 2002/0069869 | A1 | * | 6/2002 | Farmer | A61M 15/0086 | 128/203.29 |
| 2002/0078952 | A1 | * | 6/2002 | Hopper | A61F 11/00 | 128/200.24 |
| 2003/0047189 | A1 | | 3/2003 | Kumar | | |
| 2003/0168063 | A1 | | 9/2003 | Gambone | | |
| 2004/0194781 | A1 | * | 10/2004 | Fukunaga | A61M 16/01 | 128/911 |
| 2005/0092325 | A1 | * | 5/2005 | Dionne | A61M 16/08 | 128/205.25 |
| 2006/0157548 | A1 | | 7/2006 | Bastiani | | |
| 2007/0246043 | A1 | * | 10/2007 | Kwok | A61M 16/0611 | 138/119 |
| 2007/0283954 | A1 | * | 12/2007 | Dhuper | A61M 15/0086 | 128/203.15 |
| 2009/0139528 | A1 | | 6/2009 | Yevich | | |
| 2009/0211574 | A1 | * | 8/2009 | Sniadach | A61M 16/0816 | 128/207.14 |
| 2010/0024811 | A1 | | 2/2010 | Henry | | |
| 2010/0313891 | A1 | | 12/2010 | Veliss | | |
| 2011/0209701 | A1 | | 9/2011 | Derringer | | |
| 2012/0006331 | A1 | | 1/2012 | Ward | | |
| 2013/0296653 | A1 | | 11/2013 | Brown | | |
| 2014/0041673 | A1 | * | 2/2014 | Walters | A61M 16/0488 | 128/887 |
| 2014/0102452 | A1 | * | 4/2014 | Forrester | A61M 16/0875 | 128/204.18 |
| 2014/0128678 | A1 | * | 5/2014 | Kileny | A61M 16/0816 | 128/200.26 |
| 2015/0013680 | A1 | | 1/2015 | Mayo | | |
| 2015/0083121 | A1 | | 3/2015 | Fisher | | |
| 2016/0045099 | A1 | | 2/2016 | Farhadi | | |
| 2017/0367567 | A1 | | 12/2017 | Swift | | |
| 2018/0099108 | A1 | * | 4/2018 | Baek | A61M 16/0081 | |
| 2018/0134459 | A1 | * | 5/2018 | Gerami | A61M 16/0816 | |
| 2018/0214651 | A1 | | 8/2018 | McCracken | | |
| 2019/0060606 | A1 | | 2/2019 | Vazales | | |
| 2020/0023151 | A1 | | 1/2020 | Karlsson | | |
| 2020/0179633 | A1 | * | 6/2020 | Beasley | A61M 16/0875 | |
| 2021/0346629 | A1 | | 11/2021 | McLaren | | |
| 2021/0360999 | A1 | | 11/2021 | Yelkin | | |
| 2022/0000575 | A1 | | 1/2022 | Ugbeye | | |
| 2022/0265949 | A1 | * | 8/2022 | Davidson | A61M 16/0816 | |

* cited by examiner

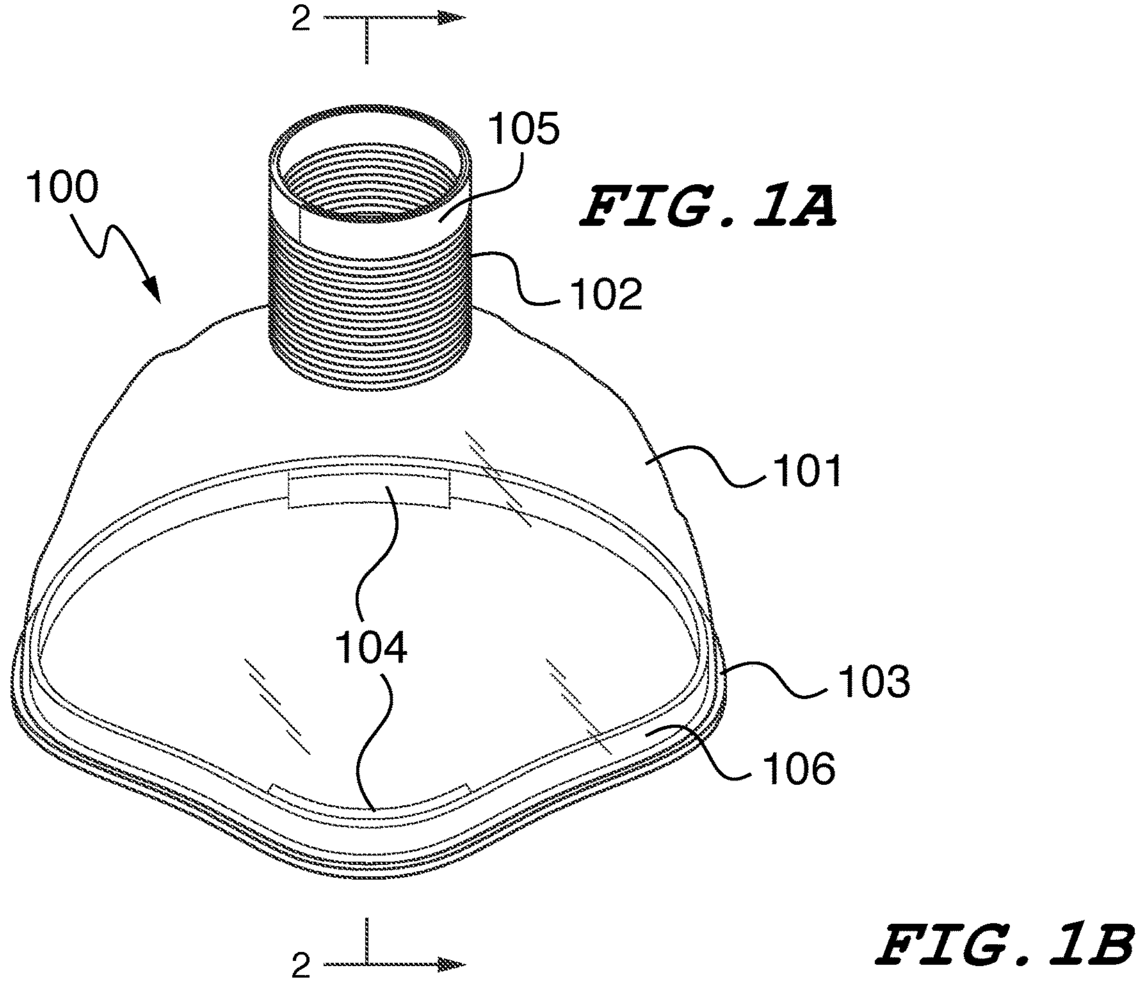
FIG. 1A
FIG. 1B
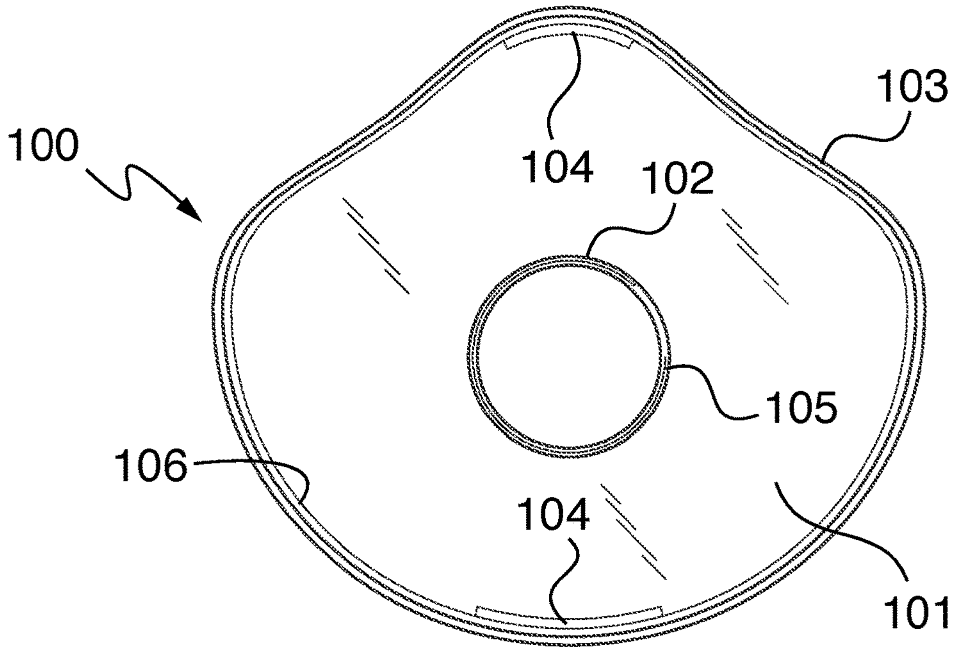

SANITARY EXTUBATION COVER AND METHOD FOR ITS USE

CROSS REFERENCE TO RELATED APPLICATIONS

U.S. provisional application 63/034,384, filed on Jun. 3, 2020, is incorporated by reference herein in its entirety. U.S. application Ser. No. 16/894,703 is incorporated by reference herein in its entirety. U.S. provisional application 63/115,069 is incorporated by reference herein in its entirety. U.S. provisional application 63/128,206 is incorporated by reference herein in its entirety.

BACKGROUND OF THE INVENTION

Field of the Invention

The present general inventive concept is directed to a method and apparatus directed to a cover for an endotracheal tube and a method for performing extubation while utilizing the cover.

Description of the Related Art

Intubation is a common medical procedure in which an endotracheal tube is placed through a patient's mouth and airway in order to place the patient on a ventilator. When the endotracheal tube is ultimately removed from the patient's mouth termed extubation, the patient commonly coughs, which could aerosolize microbes in the operating room and among the operating room staff. This is especially important during times when viruses such as COVID-19 are spreading in communities and hospitals.

What is needed is a more sanitary way to perform extubation which reduces the potential spread of contaminants.

SUMMARY OF THE INVENTION

It is an aspect of the present invention to provide a device and method to perform extubation in a more sanitary manner.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Further features and advantages of the present invention, as well as the structure and operation of various embodiments of the present invention, will become apparent and more readily appreciated from the following description of the preferred embodiments, taken in conjunction with the accompanying drawings of which:

FIG. 1A is a drawing showing a front view of a sanitary extubation cover, according to an embodiment;

FIG. 1B is a drawing showing a top view of the sanitary extubation cover, according to an embodiment;

DESCRIPTION OF THE PREFERRED EMBODIMENTS

Figure 2:
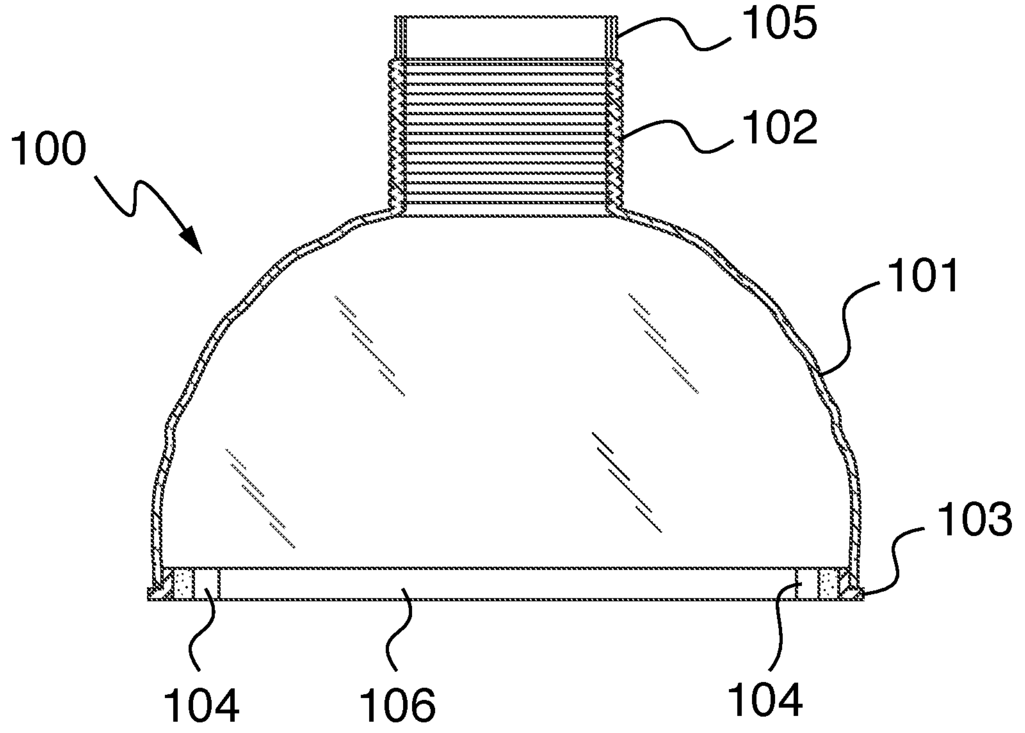
FIG. 2 is a drawing showing a cross section of the sanitary extubation cover from the view shown in FIG. 1, according to an embodiment.

Reference will now be made in detail to the presently preferred embodiments of the invention, examples of which are illustrated in the accompanying drawings, wherein like reference numerals refer to like elements throughout.

The general inventive concept relates to a method used for sanitary extubation of a patient. When an endotracheal tube is removed from a patient's mouth, the patient typically coughs. This can typically spread germs of the patient and if the patient is sick and has a transmissive disease, then the disease can spread to the personnel in the operating room. This problem is exacerbated during times of a pandemic such as COVID 19, in which operating staff is very fearful of the extubation process for this reason.

The method entails using a sanitary extubation cover which contains a mask and an attached expandable sleeve which would cover the patient's face and also the endotracheal tube. When the intubation process is complete, the sanitary extubation cover can be placed on the endotracheal tube and the mask can be secure over the patient's face. As the endotracheal tube is removed from the patient's mouth, the sleeve will expand thereby covering the endotracheal tube. If the patient coughs, the cough will be directed inside the mask, thereby containing any germs from spreading. Once the endotracheal tube is removed, the entire sanitary extubation cover (including the endotracheal tube) can be discarded in a sanitary manner. Thus, the spread of contaminants such as viruses from the extubation process has been diminished.

The sanitary extubation cover comprises a mask and a connected expandable sleeve. The mask can be form fitting in order to comfortably fit over a patient's face. The mask and attached sleeve can be made from a variety of materials (e.g., plastic, polyethylene, polyurethane, etc.) and can also come in a variety of shapes. The purpose of the mask is to cover the patient's cough, and the purpose of the sleeve is to cover the endotracheal tube so that after the extubation process, parts that came into contact with the patient are covered and can be easily and sanitarily discarded.

FIG. 1A is a drawing showing a front view of a sanitary extubation cover, according to an embodiment.

A sanitary extubation cover 100 is shown. A mask 101 is integrally attached to a sleeve 102. The sleeve 102 is cylindrical and expandable (by virtue of the sleeve 102 material being folded in the manner of an accordion) and is shown in the retracted position. The sleeve 102 can expand (see FIG. 11) to numerous times is retracted length. When expanded, the sleeve 102 unfolds (into an expanded position shown in FIG. 11) and can expand to a length a number of times its length in the retracted position (shown in FIG. 1).

A base 106 of the mask 101 can be made out of polyester, polystyrene (or any other soft material). The mask can also have a cushion (4 mm-5 mm thick) 103 (for example made of rubber, foam, sponge, plastic, cloth, etc.) at the bottom (where the mask will contact the patient's face). The mask 101 can also have pads 104 (made of foam or other soft material such as polyurethane, etc.) which will also help cushion and secure the mask 101 against the patient's face. Pads can be located, for example where the patient's mouth and chin would be. The mask 101 is typically made of a transparent material so the staff (medical personnel performing the extubation procedure) can see the patient's face at all times. The mask 101 can be made of a soft (or hard) plastic, electrostatic non-woven propylene fiber, or any suitable material which would have properties to prevent passage of microbes. and/or other unwanted particles therethrough. Note that, for example, the thickness of the material used to form the mask 101 can be, for example, 1.5 mm to 3 mm thick. The sleeve (can be transparent) 102 can be made out of a soft plastic, polyethylene, polyurethane, etc.) that can initially come folded up (in an accordion fold) and expand when pulled apart. The sleeve 102 would come integrally attached to the mask 101 using any attachment mechanism, for example the sleeve can be heat sealed together, or the sleeve can be attached using a non-toxic adhesive (e.g., rubber cement, etc.). The attachment from the sleeve 102 to the mask 101 would typically be airtight so that air cannot escape between the mask 101 and the sleeve 102. As an example, the sleeve can be made of the same material/structure as transesophageal echocardiography covers available from the EDM Medical Solutions company (clear folded up material that unfolds/stretches). Tape 105 (can be any kind of tape) is wrapped around a top or the sleeve 102 and is used to secure the sleeve 102 to the endotracheal tube. One end of the tape 105 can be peeled off the sleeve 102 while an opposing end of the tape 107 is integrally connected to the sleeve 102 and will not pull off the sleeve 102. Note that although the sleeve initially comes retracted (compressed) using an accordion fold in the material, it is noted that the sleeve can be configured to expand telescopically (as opposed to being folded up), and in fact any mechanism can be used to enable the sleeve to initially come compressed and then expand into the expanded state when needed.

The sanitary extubation cover 100 would be initially provided as a single unit self-contained as shown, Note that the sleeve is hollow and opens into the mask 101 (in other words there is no obstruction inside the sleeve (hollow) as it opens into the mask), as such air inside the mask 101 could flow into the sleeve 102 (and vice-versa).

FIG. 1B is a drawing showing a top view of the sanitary extubation cover, according to an embodiment.

The view in FIG. 1B shows the view looking into the mask 101 and then into the hollow sleeve 102.

FIG. 2 is a drawing showing a cross section of the sanitary extubation cover from the view shown in FIG. 1, according to an embodiment.

The cushion 103 is shown at the bottom of the mask 101.

Figure 3:
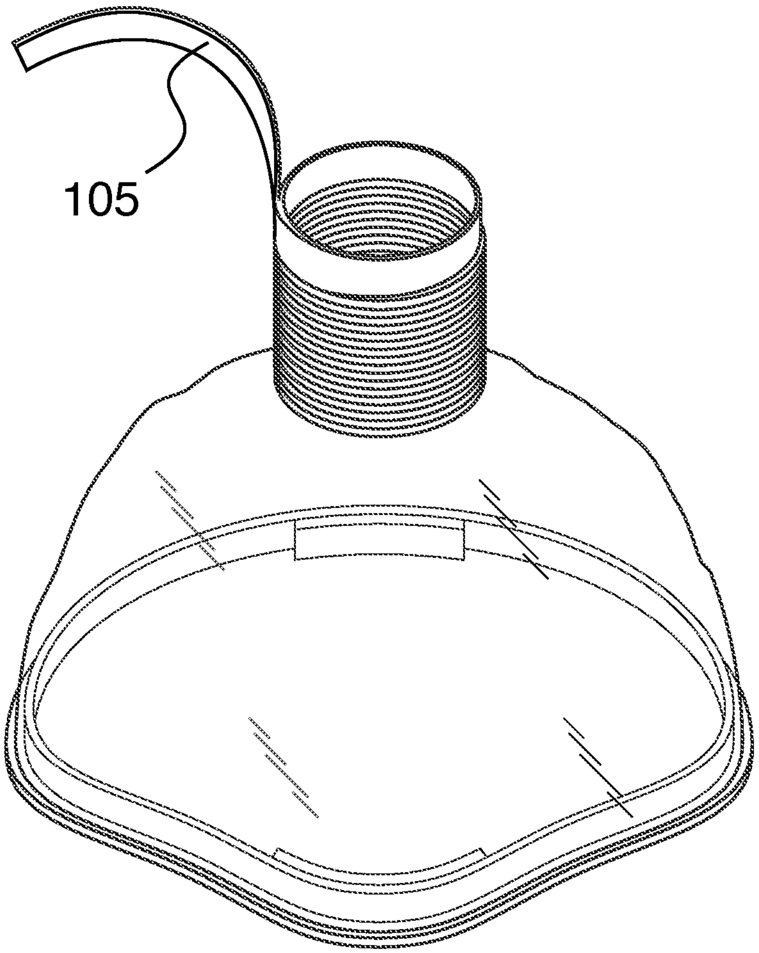
FIG. 3 is a drawing showing a front view of the sanitary extubation cover with its tape peeled off, according to an embodiment.

FIG. 3 is a drawing showing a front view of the sanitary extubation cover with its tape peeled off, according to an embodiment.

The tape 105 is shown pulled off from the top of the sleeve 102. The tape 105 is used during the extubation process (see FIG. 9). One end of the tape 105 is pulled away from the sleeve 102 while an opposite end of the tape 105 is integrally attached to the sleeve 102 and would not peel off.

Figure 4:
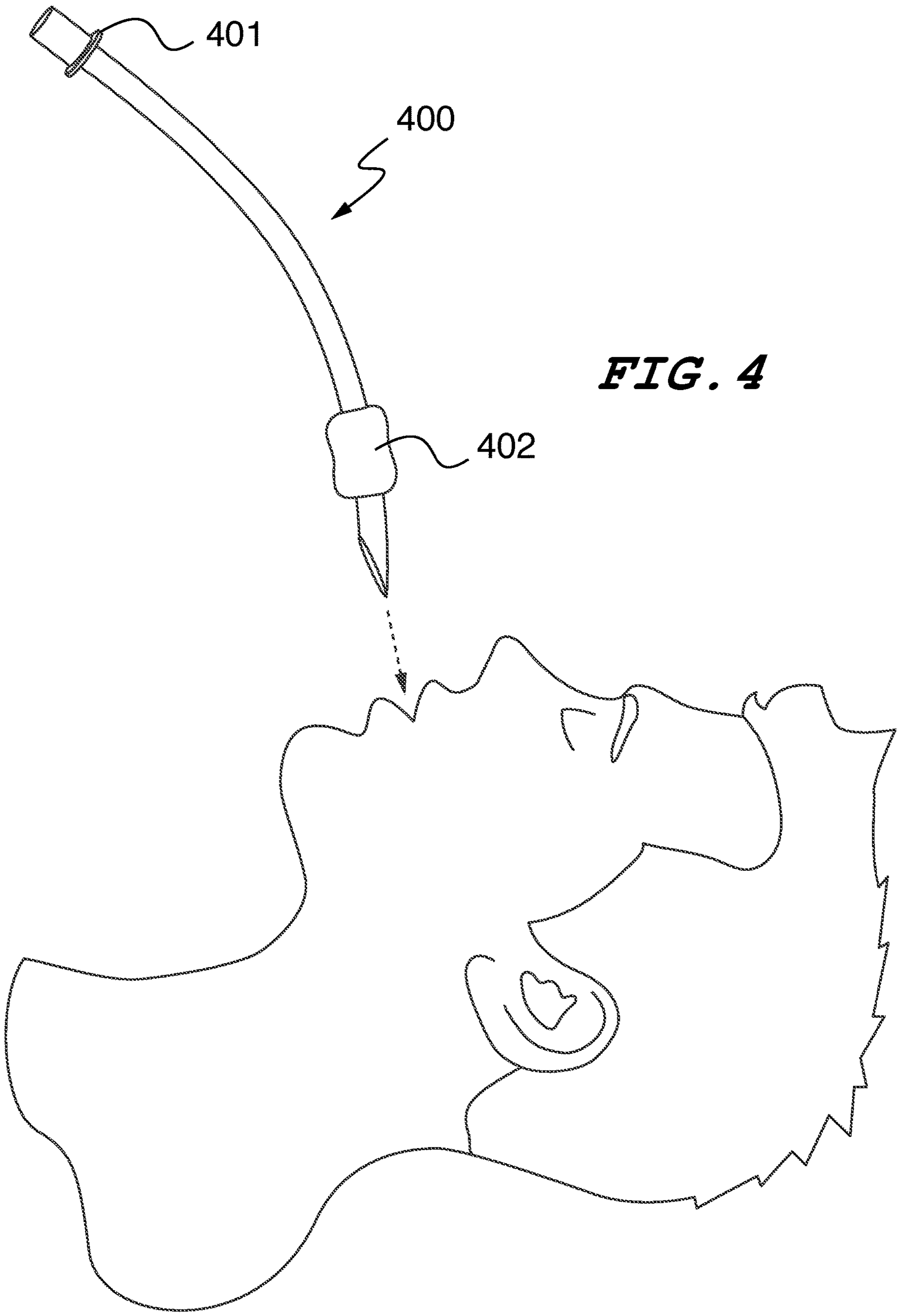
FIG. 4 is a drawing showing an endotracheal tube being inserted into a patient's mouth, according to an embodiment.

FIG. 4 is a drawing showing an endotracheal tube being inserted into a patient's mouth, according to an embodiment.

A standard endotracheal tube 400 is inserted into a patient's mouth. A connector 401 and a cuff 402 are also present on the endotracheal tube 400.

Figure 5:
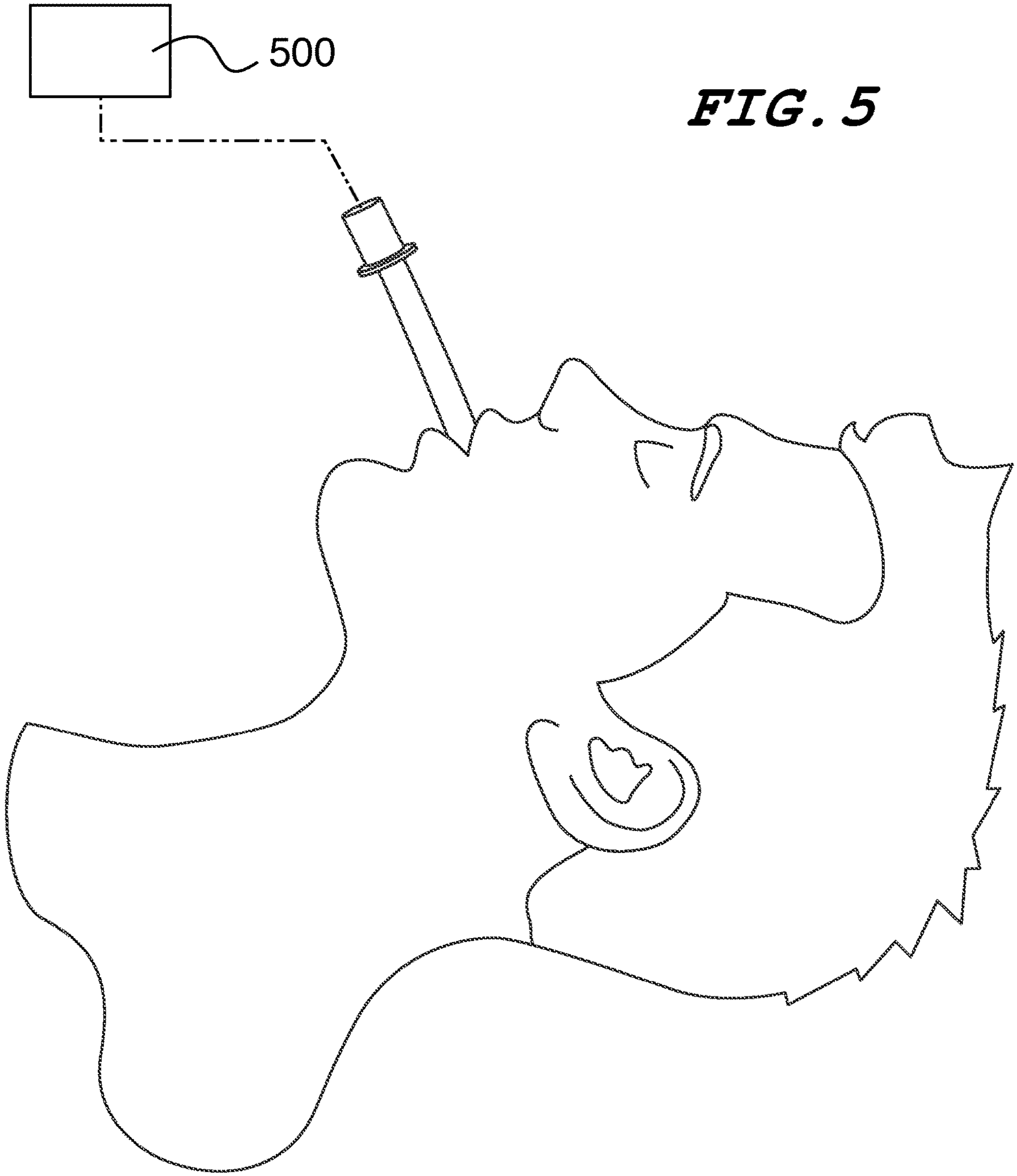
FIG. 5 is a drawing showing the endotracheal tube inserted into a patient's mouth and connected to a ventilator, according to an embodiment.

FIG. 5 is a drawing showing the endotracheal tube inserted into a patient's mouth and connected to a ventilator, according to an embodiment.

An end of the endotracheal tube 400 is connected to a ventilator 500 (circuit) in order to assist the patient with breathing.

Figure 6:
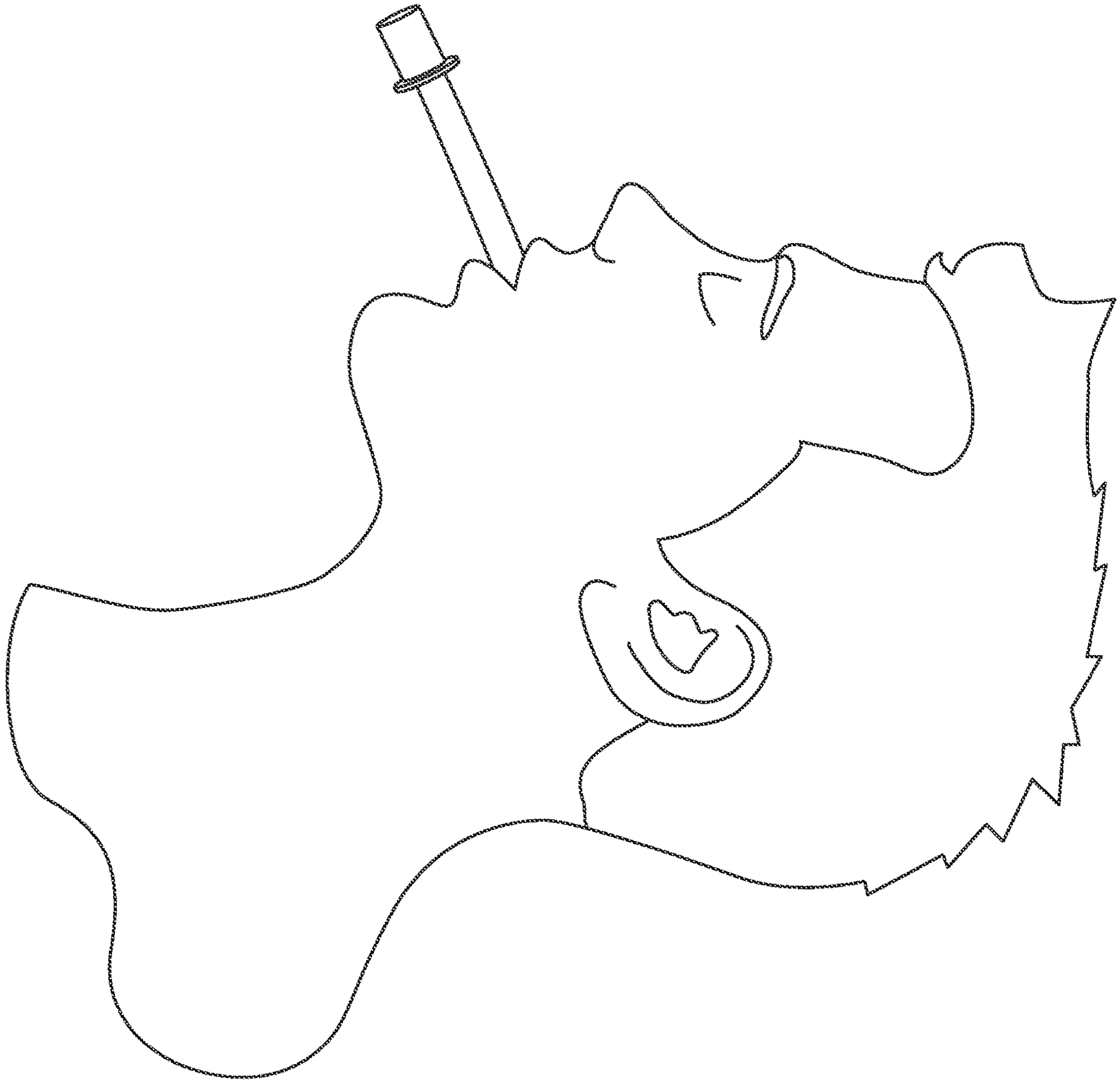
FIG. 6 is a drawing showing the endotracheal tube inserted into a patient's mouth with the ventilator disconnected, according to an embodiment.

FIG. 6 is a drawing showing the endotracheal tube inserted into a patient's mouth with the ventilator disconnected, according to an embodiment.

When whatever medical procedure that is being performing (after the patient has been intubated) has been completed, it is time to remove the endotracheal tube (extubation) using the sanitary extubation cover. The ventilator 500 is (temporarily) disconnected from the endotracheal tube 400.

Figure 7:
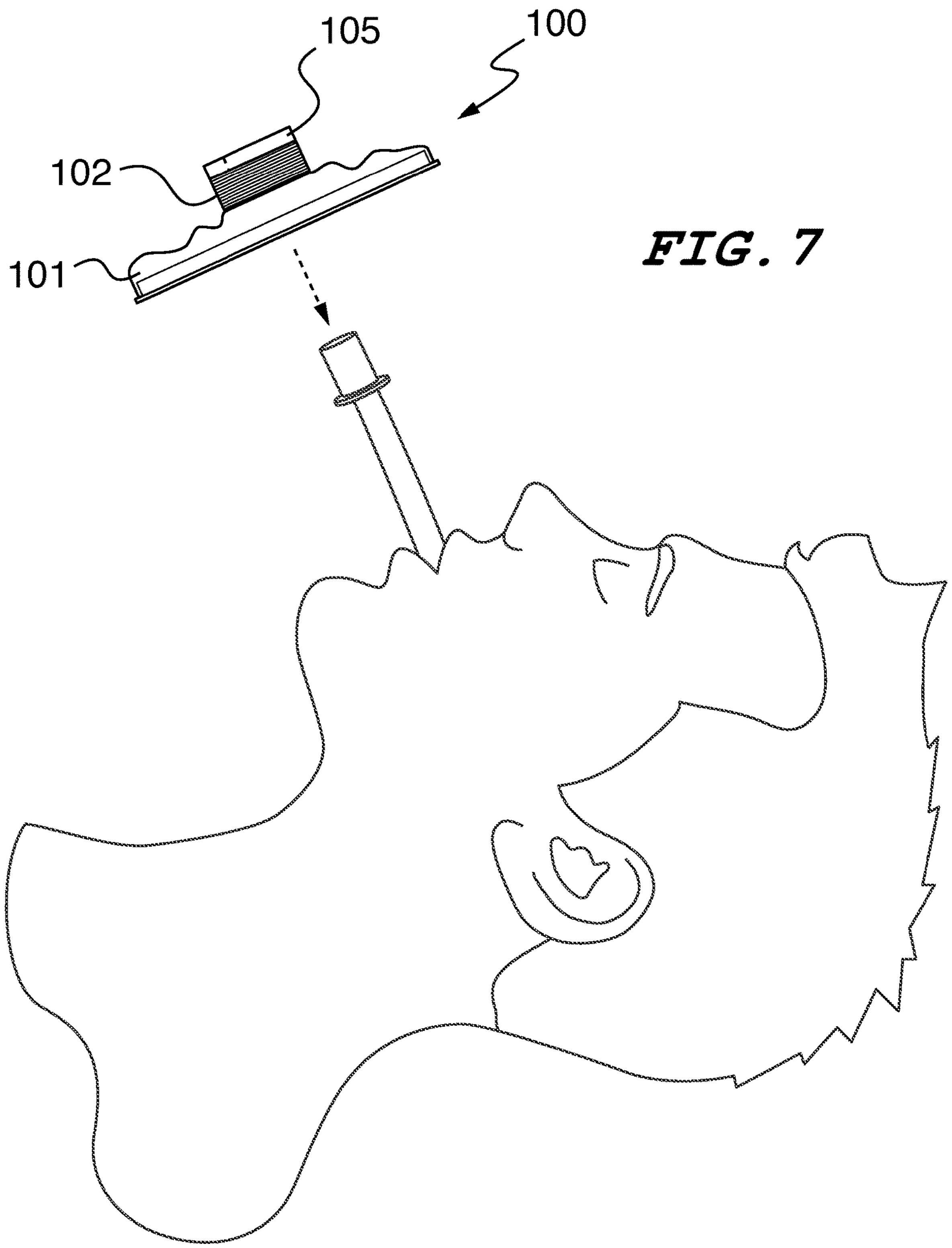
FIG. 7 is a drawing showing a sanitary extubation cover being placed over an endotracheal tube, according to an embodiment.

FIG. 7 is a drawing showing a sanitary extubation cover being placed over an endotracheal tube, according to an embodiment.

A sanitary extubation cover 700 (in its entirety) is placed onto the endotracheal tube 400. The mask 101 of the sanitary extubation cover 700 is in a compressed state (the mask 101 can be uncompressed by spreading it away from the tube 102).

Figure 8:
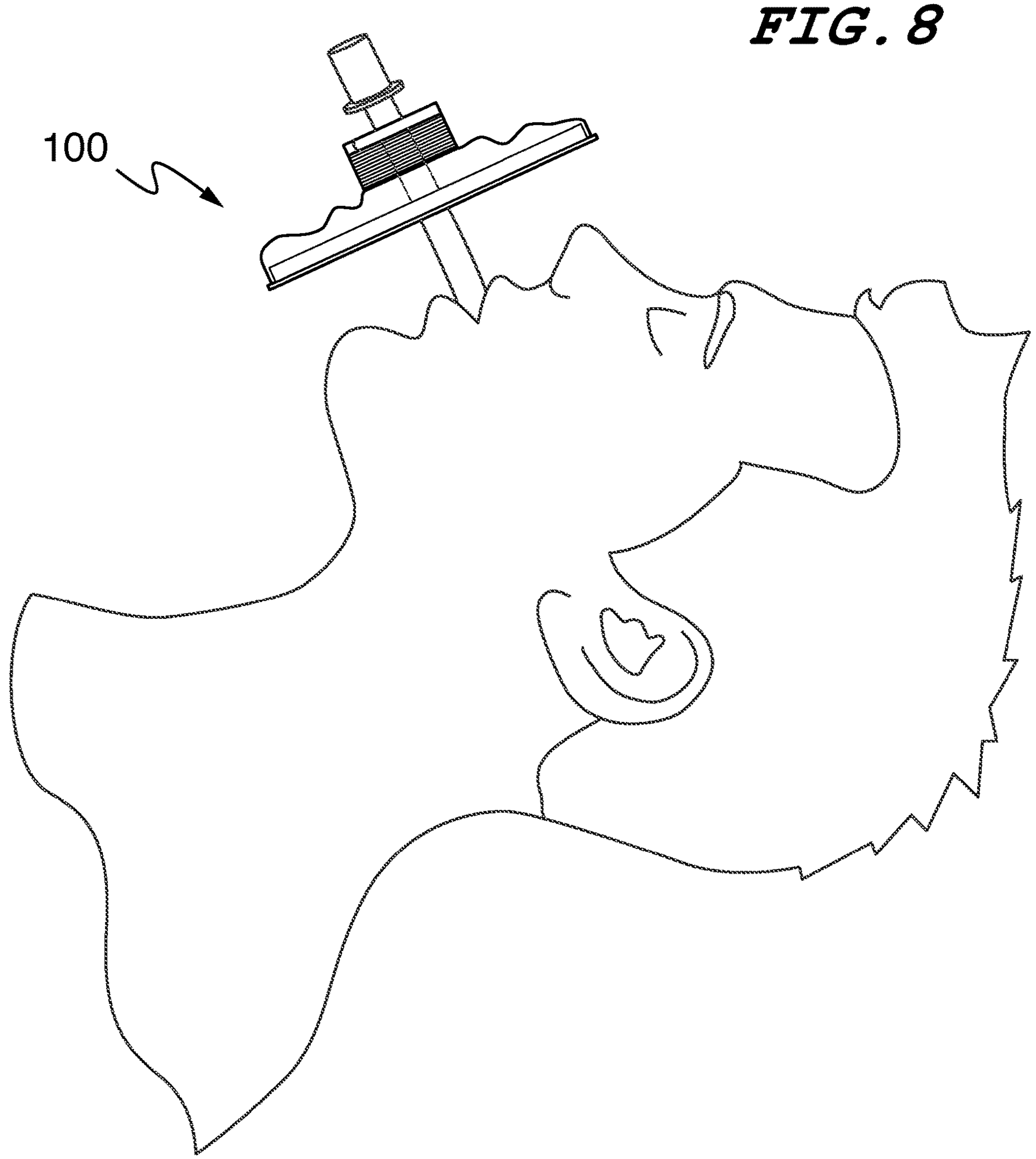
FIG. 8 is a drawing showing the sanitary extubation cover placed over an endotracheal tube, according to an embodiment.

FIG. 8 is a drawing showing the sanitary extubation cover placed over an endotracheal tube, according to an embodiment.

The sanitary extubation cover 700 is now on the endotracheal tube 400, in other words the endotracheal tube is placed through the mask 101 and sleeve 102 as shown.

Figure 9:
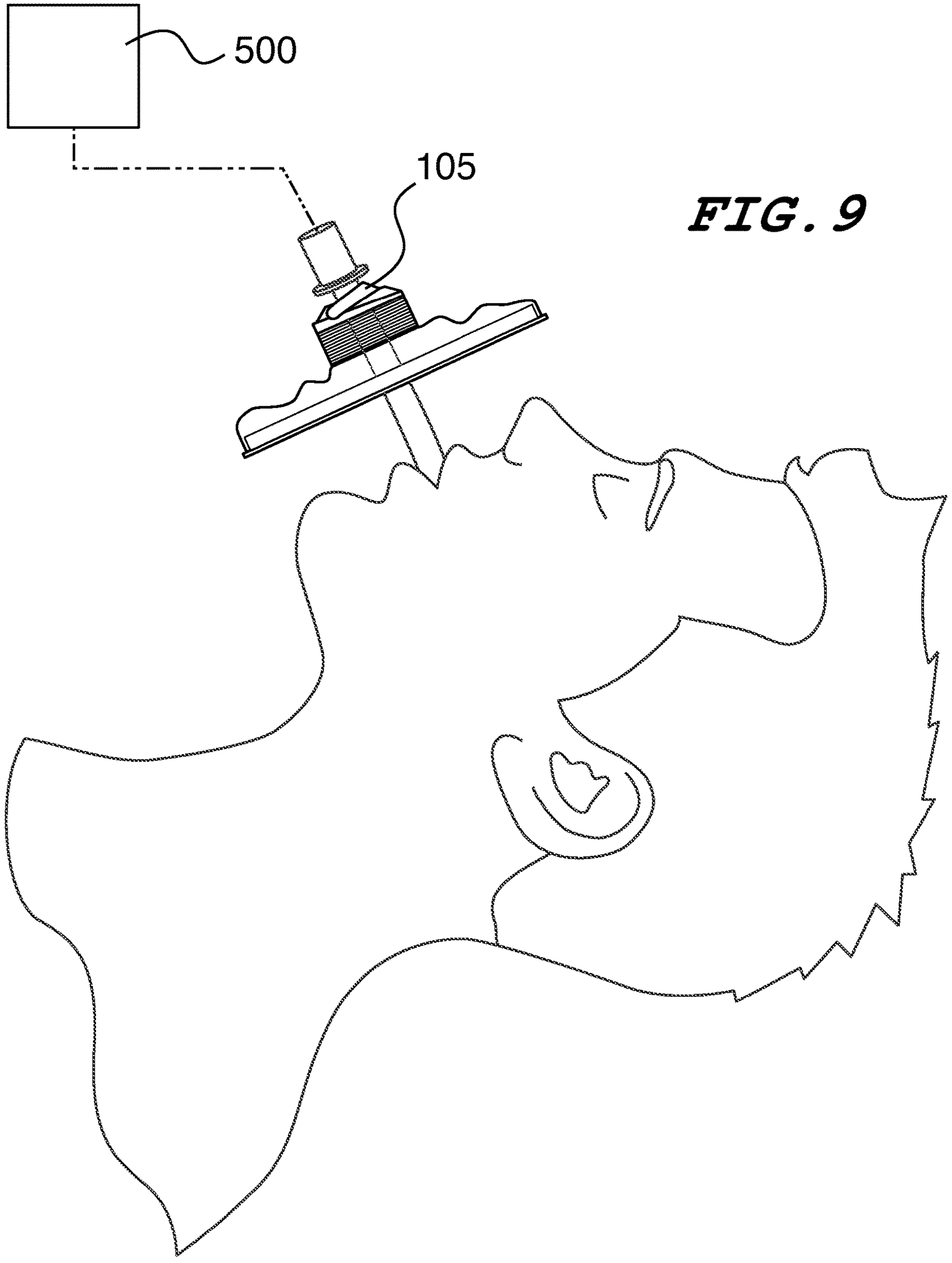
FIG. 9 is a drawing showing the sanitary extubation cover connected to a ventilator, according to an embodiment.

FIG. 9 is a drawing showing the sanitary extubation cover connected to a ventilator, according to an embodiment.

Note that the ventilator 500 is re-connected to the endotracheal tube 400. The ventilator 500 was only temporarily disconnected from the endotracheal tube 400 so that the sanitary extubation cover 100 could be placed over the endotracheal tube 400.

The tape 105 is peeled away from the sleeve 102 and wrapped around the endotracheal tube 400 so that the sleeve 102 is securely attached to the endotracheal tube 400.

Figure 10:
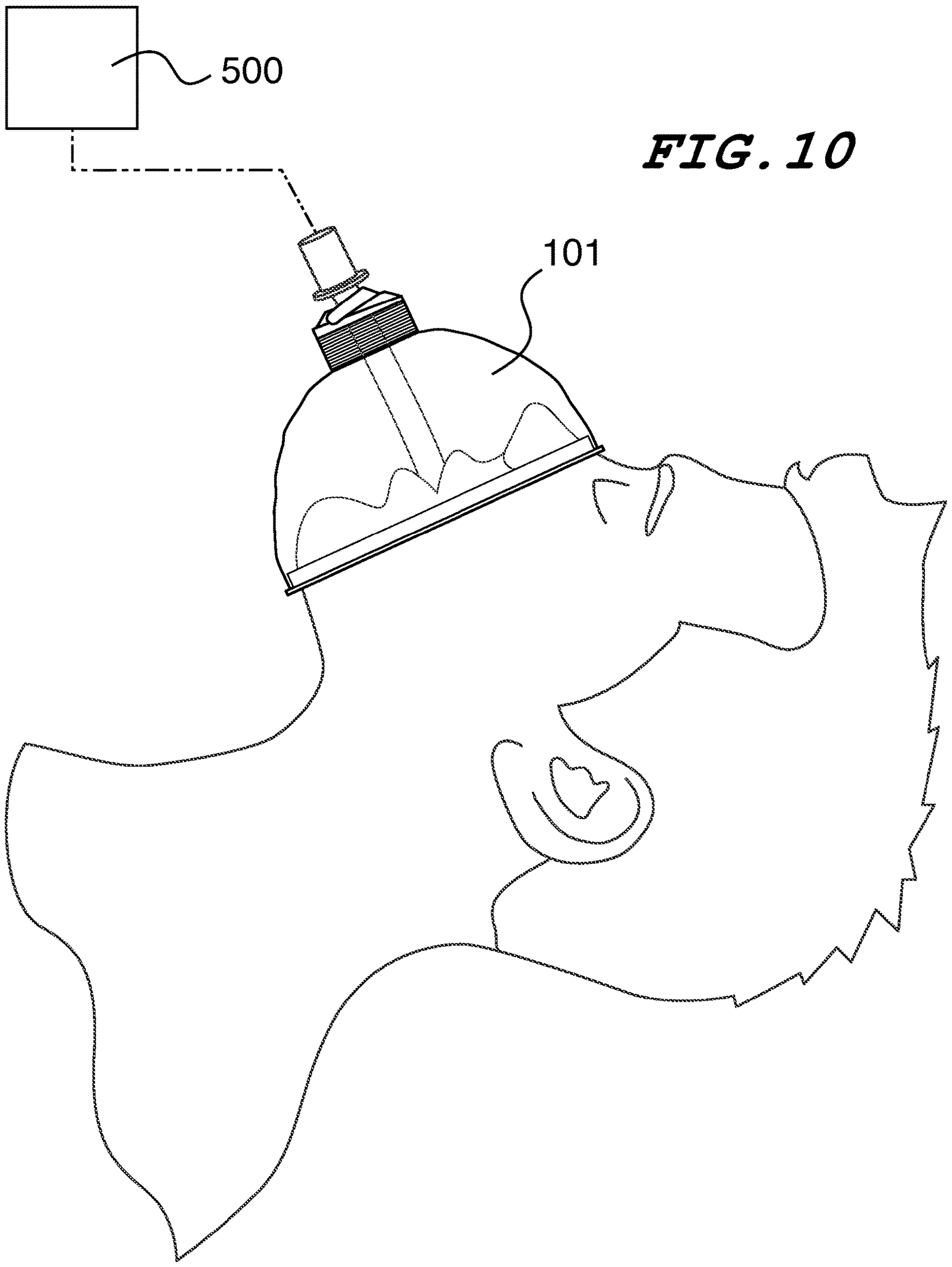
FIG. 10 is a drawing showing a mask part of the sanitary extubation cover spread over the patient's face, according to an embodiment.

FIG. 10 is a drawing showing a mask part of the sanitary extubation cover spread over the patient's face, according to an embodiment.

The mask 101 is expanded and attached to the patient's face. Tape can optionally be used to attach the mask 101 to the patient's face. The mask 101 can also be malleable (e.g., a wire on the bottom) can be molded to adjust to the patient's face. Note that when necessary, a member of the staff can manually hold the mask in place (against the patient's face) so the mask stays on the patient's face (typically while the endotracheal tube is removed from the patient's mouth).

Figure 11:
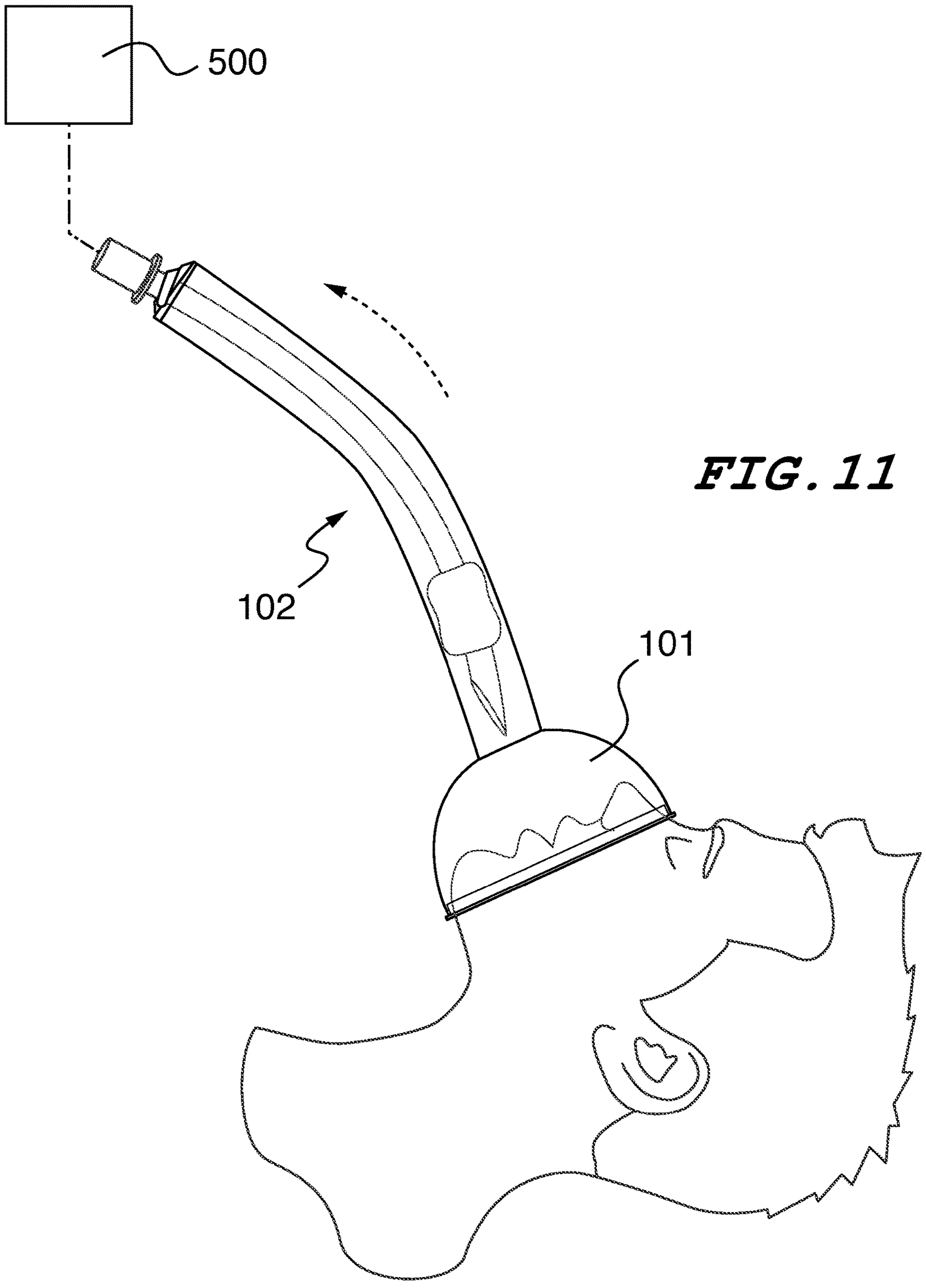
FIG. 11 is a drawing showing a sleeve of the sanitary extubation cover being expanded as the endotracheal tube is pulled out of the patient's mouth, according to an embodiment.

FIG. 11 is a drawing showing a sleeve of the sanitary extubation cover being expanded as the endotracheal tube is pulled out of the patient's mouth, according to an embodiment.

The endotracheal tube 400 is pulled out of the patient's mouth. Because the tape 105 secures the sleeve 102 to the endotracheal tube 400 and the mask 101 is secured to the patient's face, the sleeve 102 expands as the endotracheal tube 400 is being removed. Since the sleeve 102 is integrally attached to the mask 101 there is no air (and hence no contaminants) that can escape between the sleeve 102 and the mask 101. Since the bottom of the mask 101 is secured entirely to the patient's face, no air would also escape out from the mask.

Figure 12:
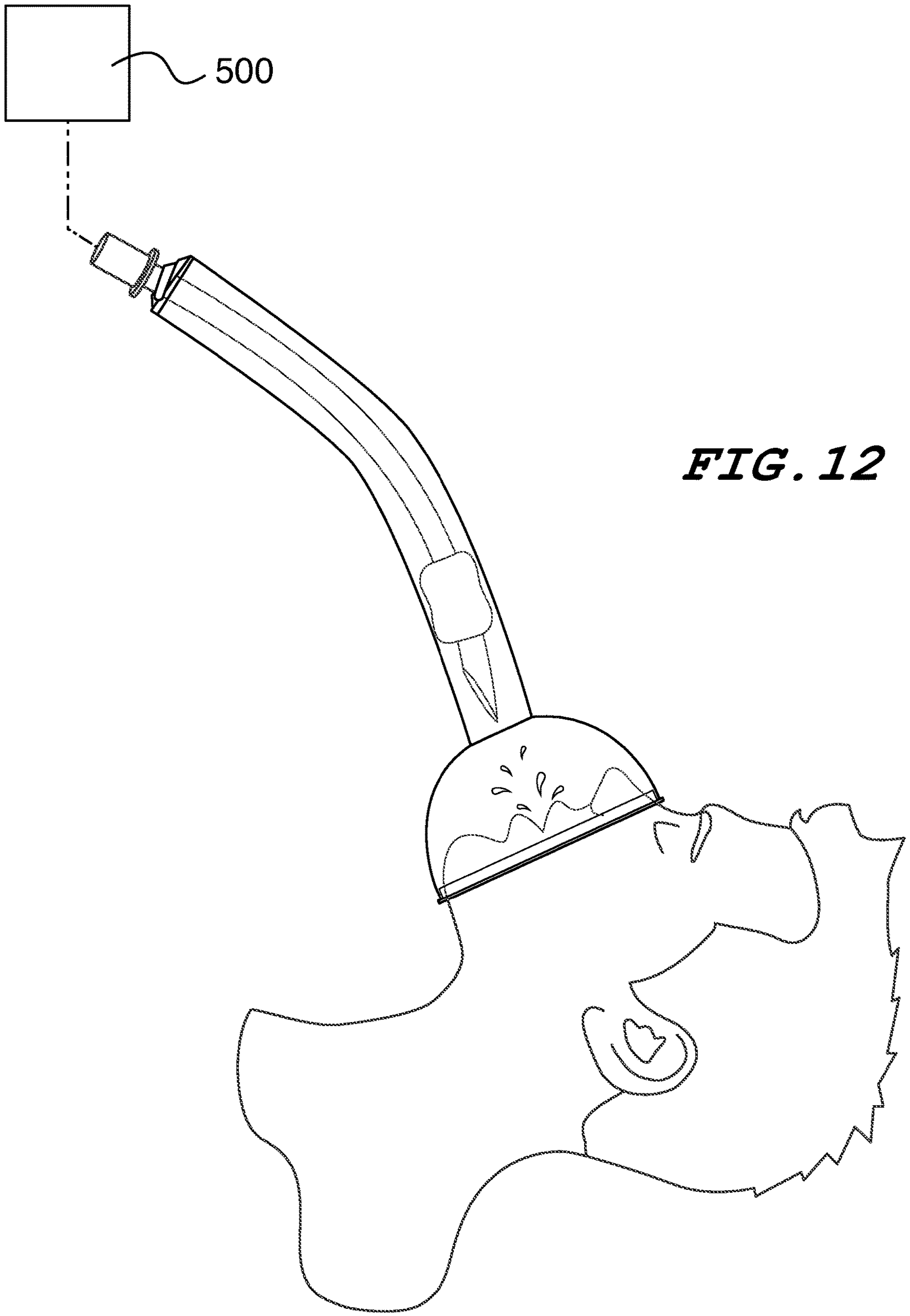
FIG. 12 is a drawing showing the patient coughing into the mask, according to an embodiment.

FIG. 12 is a drawing showing the patient coughing into the mask, according to an embodiment.

It is common that when the endotracheal tube 400 is removed from a patient, the patient would cough. The patient is shown coughing. The debris from the cough are contained inside the mask 101 (and also the sleeve 102). Note that the ventilator 500 should typically still be attached to the endotracheal tube at this time.

Figure 13:
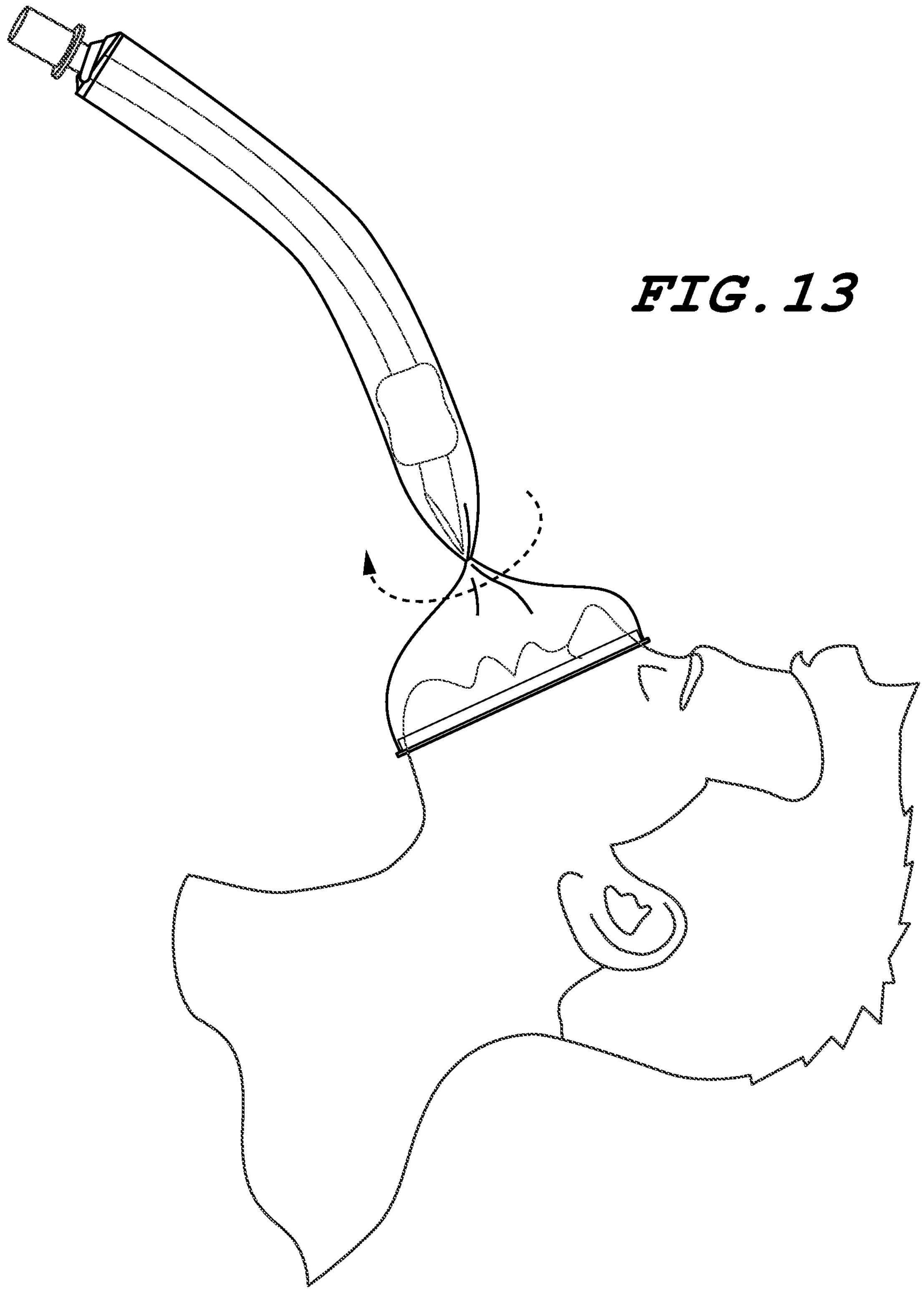
FIG. 13 is a drawing showing the sleeve being twisted to contain the endotracheal tube, according to an embodiment.

FIG. 13 is a drawing showing the sleeve being twisted, according to an embodiment.

The ventilator 500 can be disconnected from the endotracheal tube 400 at this point. The sleeve 102 can now (optionally) be twisted in order to contain endotracheal tube secretions from falling inside the mask 101 and from passing up into the sleeve 102. The mask 101 can now be removed from the patient.

Figure 14:
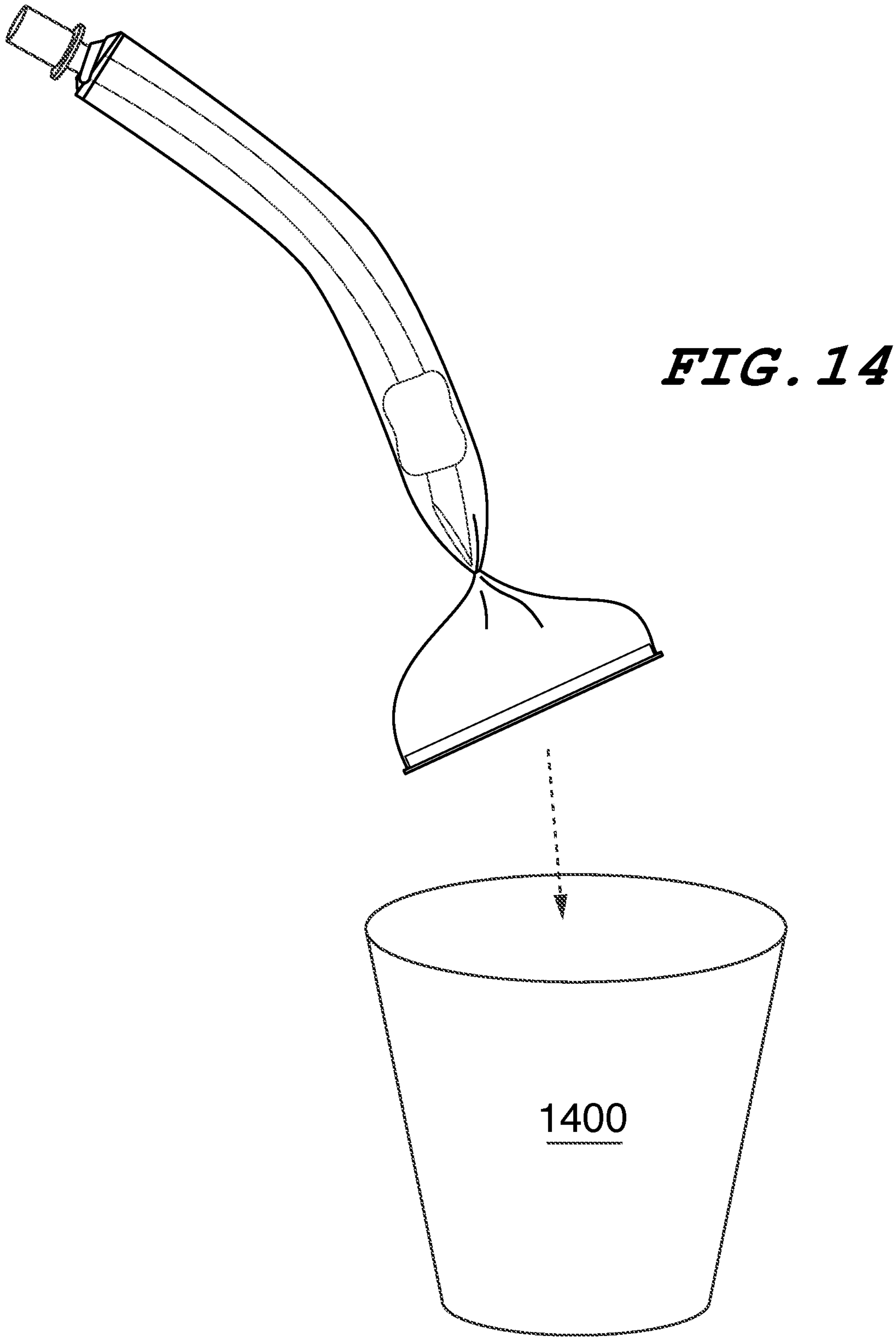
FIG. 14 is a drawing showing the sanitary extubation cover being disposed of, according to an embodiment.

FIG. 14 is a drawing showing the sanitary extubation cover being disposed of, according to an embodiment.

The entire sanitary extubation cover 100 is now disposed of in a trash can 1400. It can also be disposed of inside a garbage bag (not pictured) which can be sealed once it contains the entire sanitary extubation cover 100.

Figure 15:
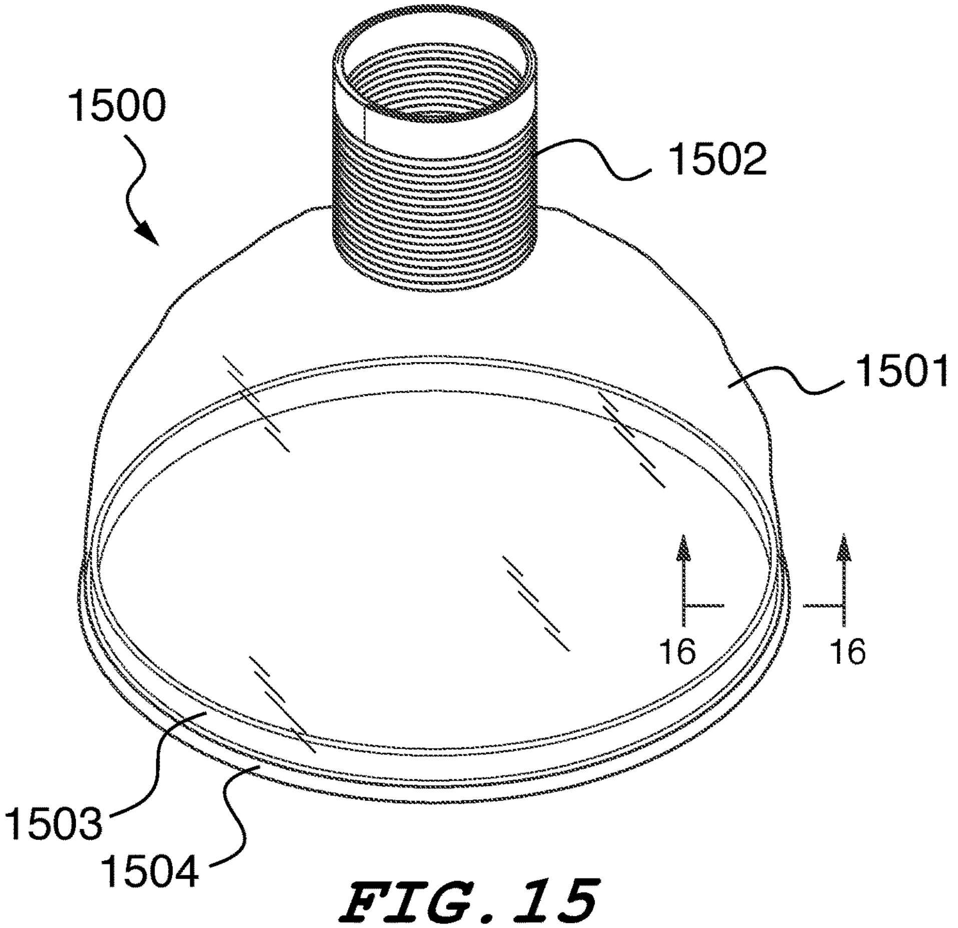
FIG. 15 is a drawing showing another embodiment of a sanitary extubation cover, according to an embodiment.

FIG. 15 is a drawing showing another embodiment of a sanitary extubation cover, according to an embodiment.

In another embodiment, a sanitary extubation cover 1500 can be the same (and operate the same) as the previously discussed sanitary extubation cover 100 (including the sleeve 1502). The mask 1501 can have a circular (does not need to be perfectly circular) foam pad 1503 to provide cushioning against the patient's face and a circular (does not need to be perfectly circular) coated wire 1504 (with wire inside) at the bottom of the mask which can be malleable and can help confirm the mask 1501 to the patient's face.

Figure 16:
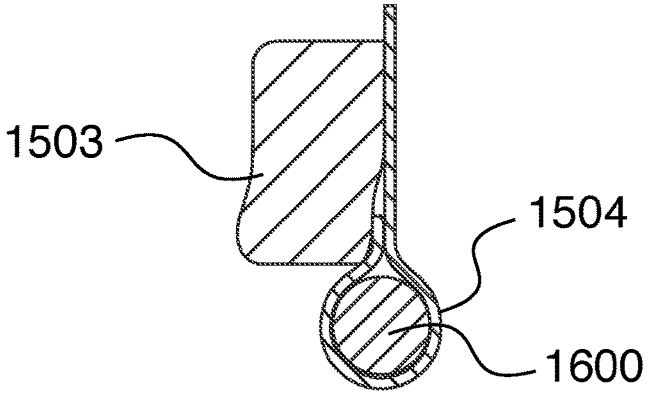
FIG. 16 is a drawing showing a cross section of the sanitary extubation cover from the view shown in FIG. 15, according to an embodiment.

FIG. 16 is a drawing showing a cross section of the sanitary extubation cover from the view shown in FIG. 15, according to an embodiment. The cross section shown in FIG. 16 is what surrounds the entire bottom perimeter of the mask 1501.

The foam pad 1503 and the wire coating 1504 surrounds a perimeter of the bottom of the mask 1501. The wire coating 1504 surrounds the wire 1600 so that the wire 1600 does not have to come in direct contact with the patient's face. The wire coating can be rubber, cloth, nylon, plastic, etc. The wire can be any type of wire (e.g., copper, iron, steel, brass, bronze, etc.)

Figure 17:
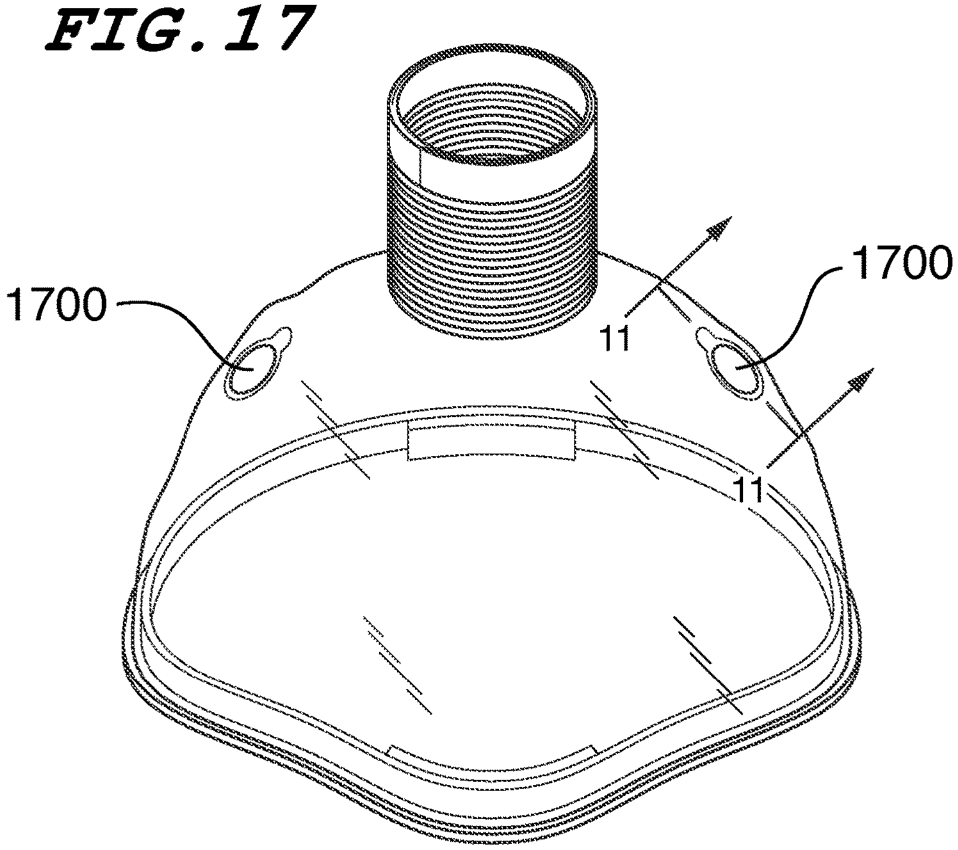
FIG. 17 is a drawing showing portholes in a sanitary extubation cover, according to an embodiment.

FIG. 17 is a drawing showing portholes in a sanitary extubation cover, according to an embodiment.

During the extubation process, suction may be applied to the patient's mouth in order to suction out any excess saliva. This can be done by a suction device which uses a catheter or wand which operates as a kind of vacuum cleaner. Portholes 1700 can be provided in order to enable a suction device (not pictured in FIG. 17) to enter the mask for the purpose of suctioning the patient's mouth. Since the mask is made of transparent material, the staff can easily place the suction device through one of the two portholes 1700 and suction the patient/s mouth and face and then remove the section device.

Figure 18:
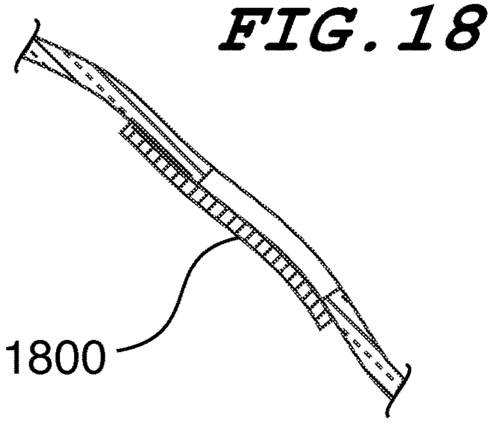
FIG. 18 is a cross section of the sanitary extubation cover from the view shown in FIG. 17 in the closed position, according to an embodiment.

FIG. 18 is a cross section of the sanitary extubation cover from the view shown in FIG. 17 in the closed position, according to an embodiment.

In the closed position, a flap 1800 seals against the porthole 1700 thereby creating an airtight seal.

Figure 19:
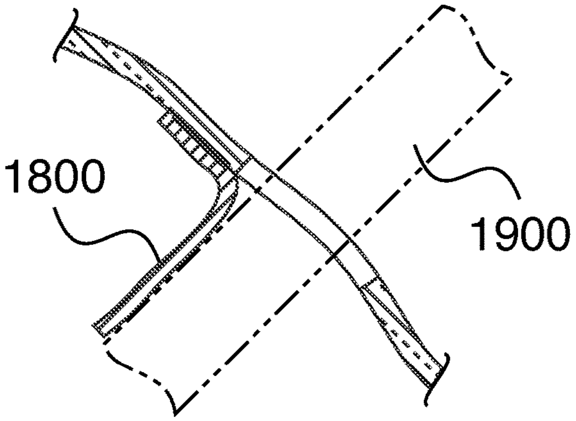
FIG. 19 is a cross section of the sanitary extubation cover from the view shown in FIG. 17 in the open position, according to an embodiment.

FIG. 19 is a cross section of the sanitary extubation cover from the view shown in FIG. 17 in the open position, according to an embodiment.

When a suction device 1900 is inserted through a porthole 1700, then the flap 1800 is pushed open into an open position, thereby allowing the suction device 1900 to enter the mask in order to suction the inside of the mask and patient's mouth. When the suction device 1900 is removed, the flap 1800 would automatically spring back into the closed position.

Figure 20:
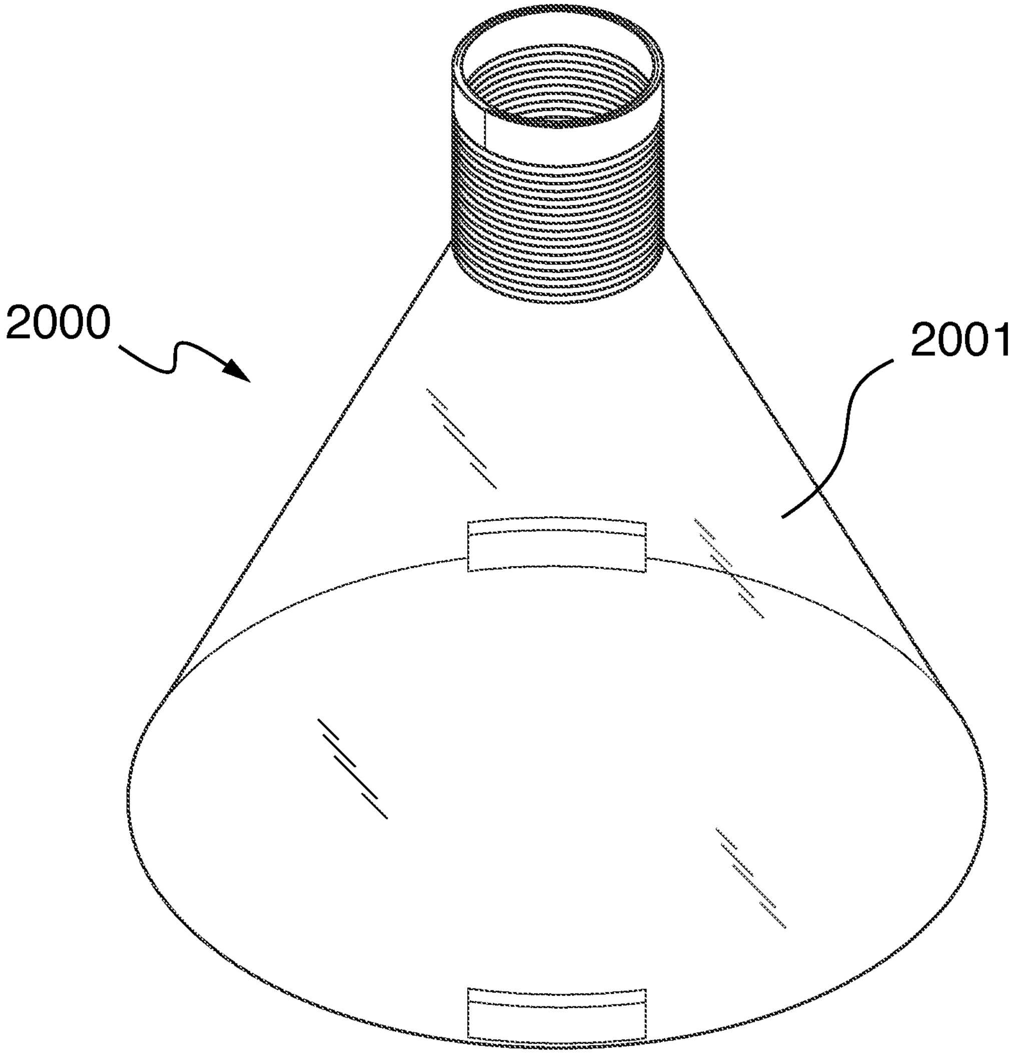
FIG. 20 is a drawing showing a further embodiment of a sanitary extubation cover, according to an embodiment.

FIG. 20 is a drawing showing a further embodiment of a sanitary extubation cover, according to an embodiment.

In a further embodiment, a mask portion 2001 of a sanitary extubation device 2000 can be conical shaped, but otherwise be structured and operate as described herein.

Figure 21:
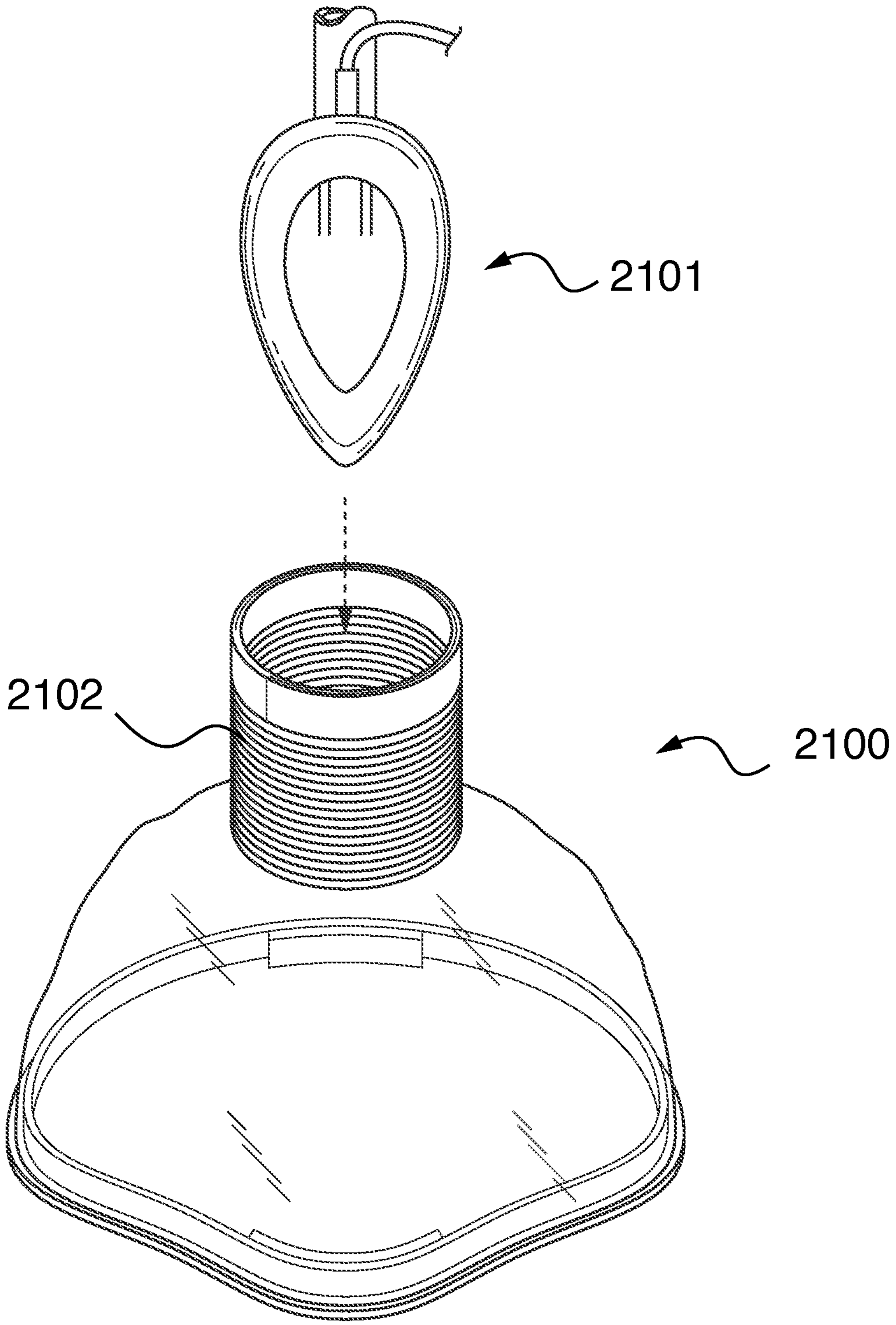
FIG. 21 is a drawing showing a sanitary extubation cover being used with a laryngeal mask airway, according to an embodiment.

FIG. 21 is a drawing showing a sanitary extubation cover being used with a laryngeal mask airway, according to an embodiment.

A sanitary extubation cover 2100 can be structured and operate as described herein but the sleeve 2102 can be sized (e.g., larger) for use with a laryngeal mask airway (LMA) 2101 instead of an endotracheal tube. However, the structure and operation of the sanitary extubation cover would otherwise remain the same.

Figure 22:
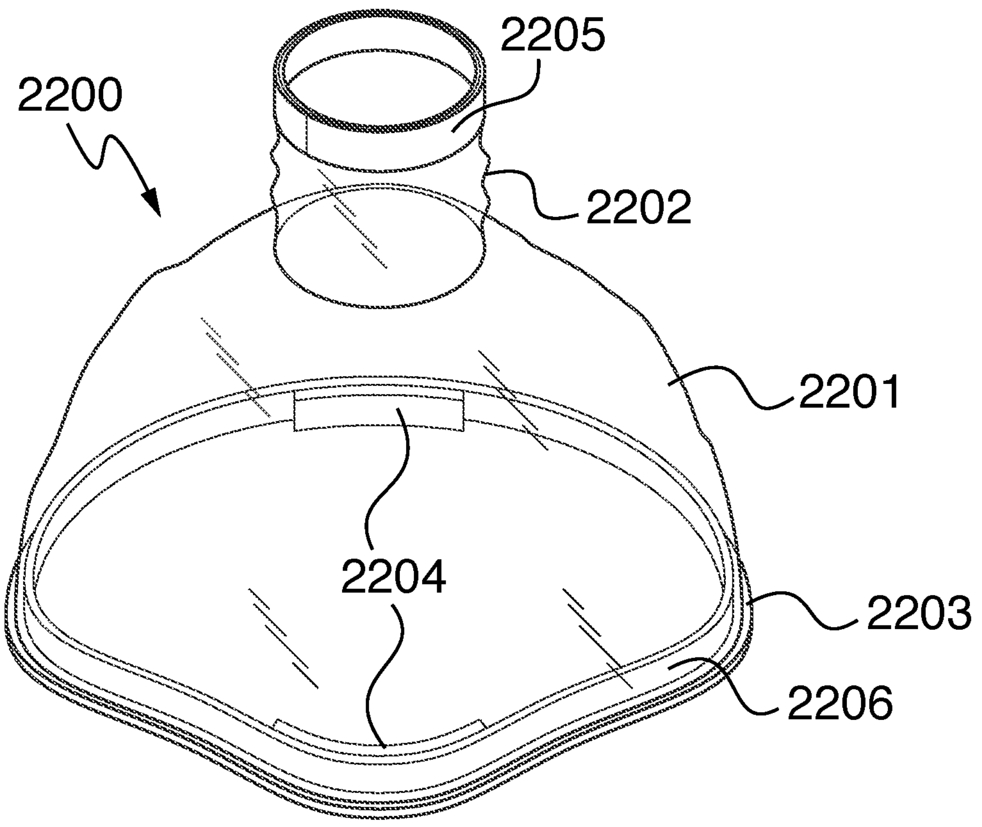
FIG. 22 is a drawing showing a sanitary extubation cover with a rubber sleeve 2202, according to an embodiment.

FIG. 22 is a drawing showing a sanitary extubation cover with a rubber sleeve 2202, according to an embodiment.

Instead of a folded sleeve as discussed herein, a stretchable sleeve 2202 can be utilized which is made out of rubber which would stretch (expand) when pulled. This embodiment is structured and operates the same way as the other embodiments discussed herein, with the only difference that the sleeve 2202 would be made out of rubber or other stretchable material. The rubber can be any type of rubber or other stretchable material, for example natural rubber, synthetic rubber, vulcanized rubber, neoprene, silicone rubber, thin latex, polyurethane, polyisoprene, etc. The stretchable material used would have to have the property of being easily stretchable, for example from 2 cm (in the retracted position) to 44 cm (in the expanded position) without breaking.

Figure 23A:
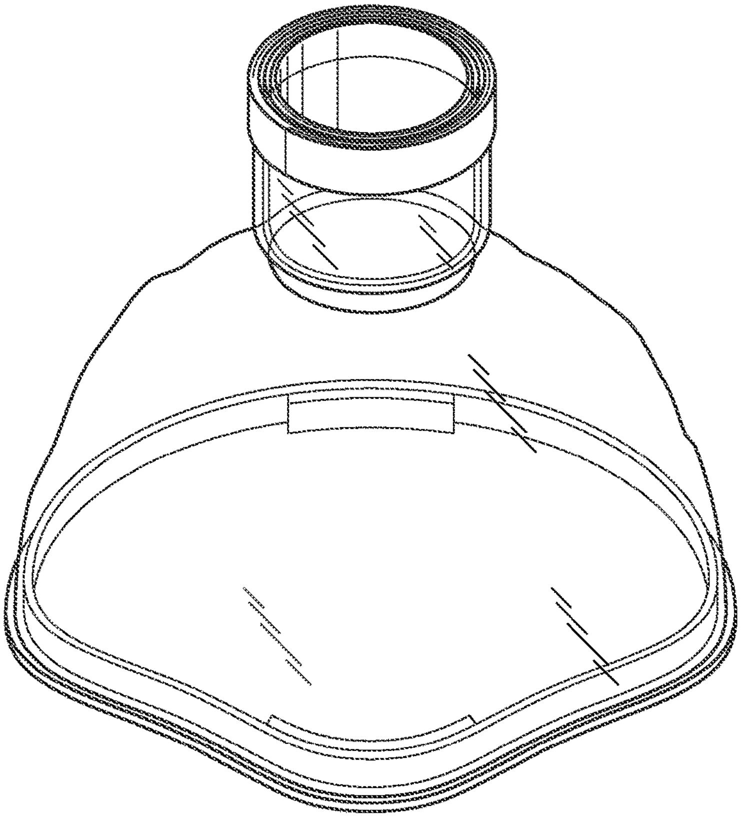
FIG. 23A is a drawing showing a sanitary extubation cover with a telescoping sleeve, according to an embodiment.

FIG. 23A is a drawing showing a sanitary extubation cover with a telescoping sleeve, according to an embodiment.

As opposed to the unfolding sleeve illustrated in FIG. 1A, a telescoping sleeve can be utilized as well as shown in FIG. 23A. The sleeve is compressed/folded vertically.

Figure 23B:
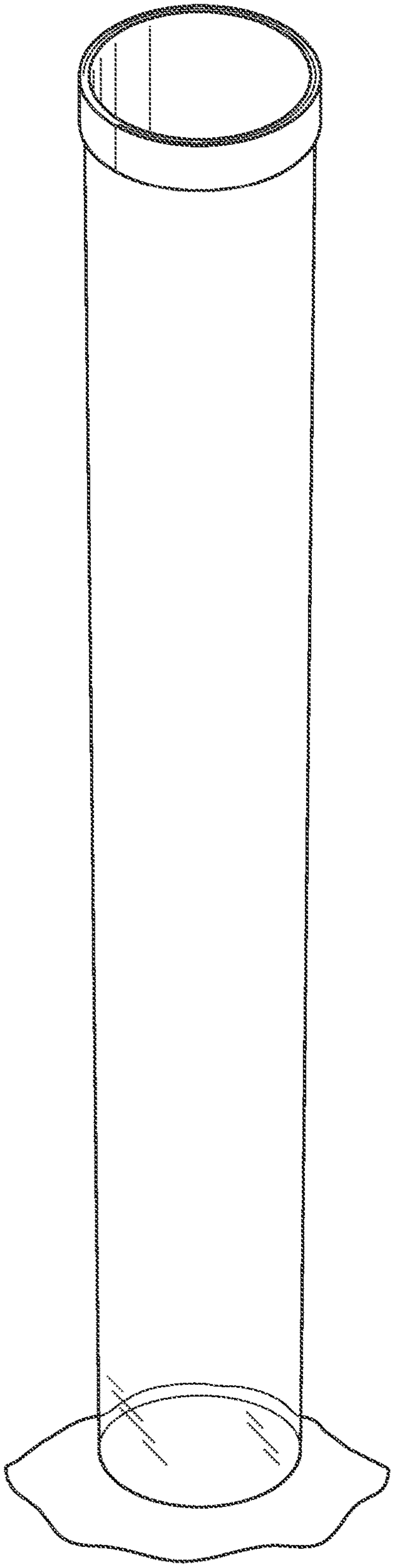
FIG. 23B is a drawing showing a sanitary extubation cover with a telescoping sleeve in an extended position, according to an embodiment.

FIG. 23B is a drawing showing a sanitary extubation cover with a telescoping sleeve in an extended position, according to an embodiment.

The telescoping sleeve is extended as shown in FIG. 23B by pulling the top of sleeve outward.

Figure 24A:
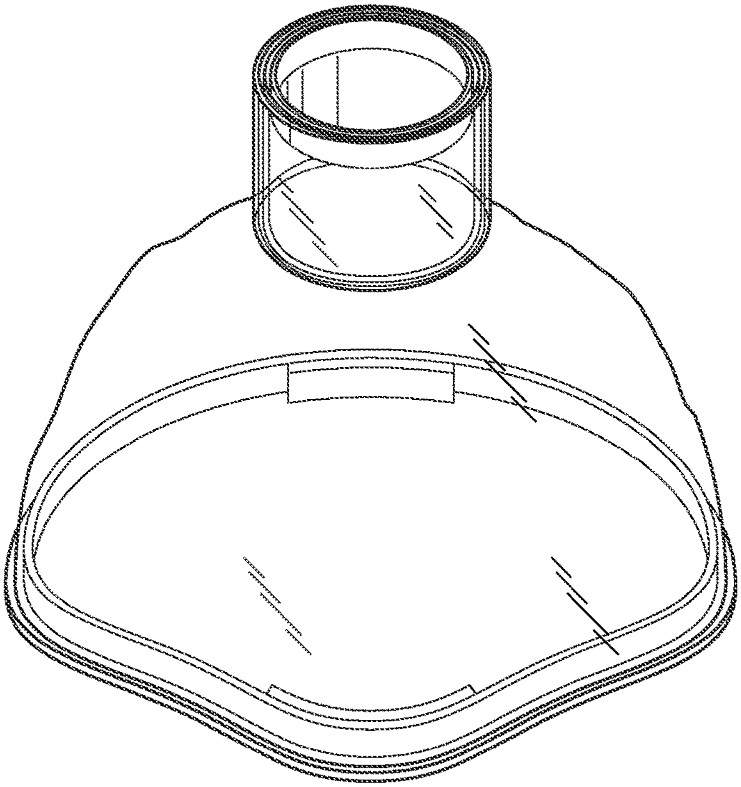
FIG. 24A is a drawing showing a sanitary extubation cover with another type of telescoping sleeve, according to an embodiment.

FIG. 24A is a drawing showing a sanitary extubation cover with another type of telescoping sleeve, according to an embodiment.

Figure 24B:
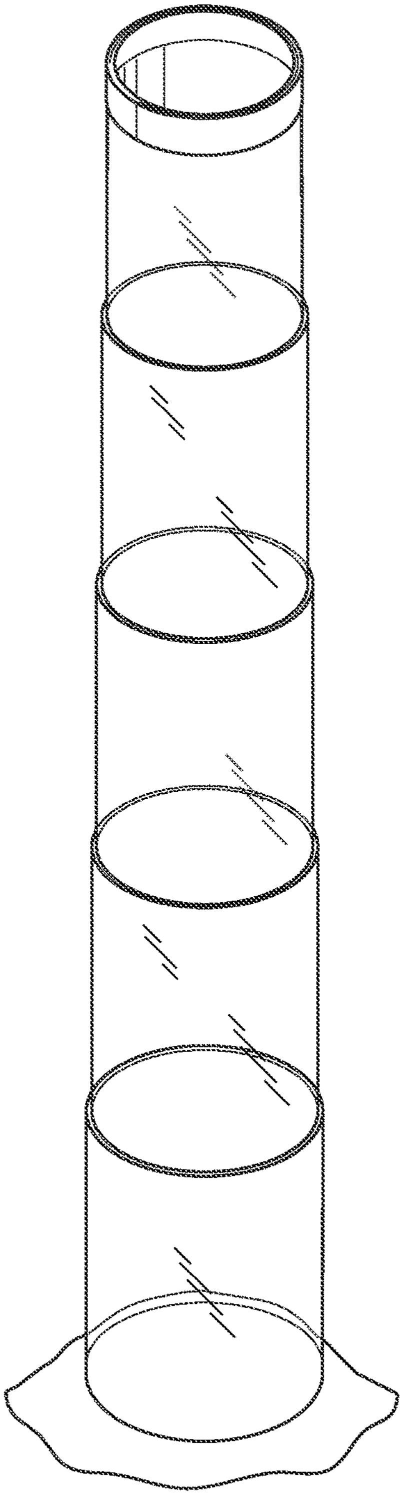
FIG. 24B is a drawing showing a sanitary extubation cover with another type of telescoping sleeve in an extended position, according to an embodiment.

This telescoping sleeve is made of tightly fit sections (typically plastic) which can fold up (as shown in FIG. 24A) and unfold (as shown in FIG. 24B).

FIG. 24B is a drawing showing a sanitary extubation cover with another type of telescoping sleeve in an extended position, according to an embodiment.

To go from the retracted position (FIG. 24A) into the extended position (FIG. 24B), the sleeve simply needs to be pulled outwards. A tight fit of the sections (e.g., friction fit) would prevent this telescoping sleeve (shown in FIG. 24B) from naturally collapsing back on itself.

The telescoping sleeve shown in FIG. 23A, FIG. 23B, 24A, 24B can be sized and operate the same as described herein with respect to the sleeve described herein (e.g., FIGS. 1A, 11-14, etc.) Note that the telescoping sleeves can all be malleable, bend and swerve (as the sleeve described herein and shown in FIGS. 1A, 11-14, etc.) in order to accommodate an endotracheal tube as shown in FIG. 11.

Figure 25:
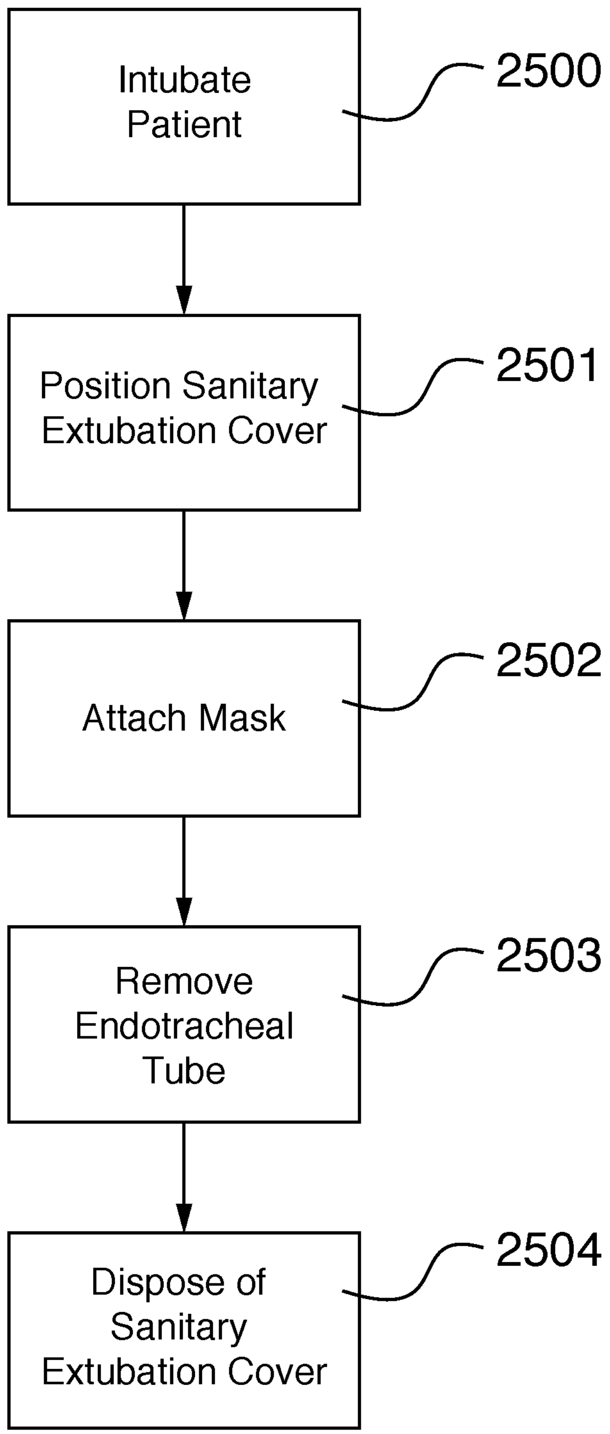
FIG. 25 is a flowchart showing operations in a method to perform extubation using a sanitary extubation cover, according to an embodiment.

FIG. 25 is a flowchart showing operations in a method to perform extubation using a sanitary extubation cover, according to an embodiment.

The method can begin with operation 2500, wherein the patient is intubated and the medical procedure is performed. This can be illustrated by FIG. 5.

From operation 2500, the method proceeds to operation 2501, wherein a sanitary extubation cover is inserted over the endotracheal tube.

This is accomplished by first disconnecting (FIG. 6) the ventilator from the endotracheal tube (briefly) and putting the sanitary extubation cover over the endotracheal tube (FIGS. 7-8). The ventilator can then be reconnected to the endotracheal tube (FIG. 9). The tape (part of the sanitary extubation cover) can be unwrapped around the sleeve and wrapped around the endotracheal tube in order to (firmly) attach the sleeve (and hence the mask since the mask is connected to the sleeve) to the endotracheal tube.

From operation 2501, the method proceeds to operation 2502, wherein the mask is unfolded and attached to the patient's face.

The mask should be attached to the patient's face (see FIG. 10). Tape (or another adhesive) can optionally be used to attach the mask to the patient's face (note this is not the same as tape 105 which is used to attach the sleeve to the endotracheal tube). Additionally (or alternatively) the bottom of the mask can be fitted around the patients face (using wire/coated wire or other malleable structure on the mask) to make a good fit.

From operation 2502, the method proceeds to operation 2503, wherein the endotracheal tube is removed from the patient's mouth. An end (the end attached to the ventilator) is pulled away from the patient's face. The tape holds the sleeve to the endotracheal tube and hence the sleeve would pull along with the end of the endotracheal tube thereby expanding the sleeve (see FIG. 11). As the end is being pulled out of the patient's mouth, a staff member (part of the team performing the extubation/medical procedure) can also hold the mask in place (against the patient's face) to ensure the mask stays on the patient's face. As the staff member pulls out the endotracheal tube, the staff member can optionally also grab and end of the sleeve (the end with the tape) to ensure the sleeve pulls along with the end of the endotracheal tube (thereby causing the sleeve to expand). As the endotracheal tube is pulled out of the patients mouth, because an end of the sleeve is secured (via tape) to the endotracheal tube and the mask is secured (and/or held) to the patient's face, the increasing distance between the mask and the end of the sleeve will cause the sleeve to unfold (or stretch) from its compressed (retracted) state (see FIG. 1) into its expanded state (see FIG. 11).

At this point (the sleeve is in the expanded position as in FIG. 12), the patient may cough. Debris from the cough would be contained inside the mask and possibly the sleeve as well but would not enter the open air of the room.

From operation 2503, the method proceeds to operation 2504, wherein the entire sanitary extubation cover is discarded.

The sleeve can optionally be twisted (as shown in FIG. 13) in order to seal the contents inside the sleeve. The entire sanitary extubation cover can then be thrown in a waste basket or in a trash bag (which can be sealed once the sanitary extubation cover is put inside the trash bag thereby keeping the contents therein contained and any contaminants inside would spread in the open air).

Note the method does not have to be implemented exactly as described, and one of ordinary skill in the art would recognize there can be other workflows to accomplishing the sanitary removal of an endotracheal tube as well using the apparatus' described herein.

Note that as one example, the following dimensions for the different parts can be used. In FIG. 1, the foam pads can be 9 cm long, 2 cm wide, and 0.25 cm thick. A width of the tape can be 0.5 to 1 cm, and a length of the tape can be 7.5 cm. A width (diameter) of the sleeve (which is cylindrical) can be for example 5-6 cm. The height of the sleeve (in the compressed state such as illustrated in FIG. 1 can be 2 cm (or range 1 cm to 3 cm), while the height of the sleeve in the stretched state such as illustrated in FIG. 11 can be 44 cm (25 cm to 50 cm). The thickness of the material used to make (any kind of) sleeve can be 1.5 mm to 3 mm thick (or even thinner and/or thicker than this). The ratio of the length of extended sleeve to the length of the compressed sleeve could be at least 9 (in other words the sleeve would extend (in the extended state) at least 8 times the length of the sleeve in the compressed state). When the mask 101 is expanded, a distance from the bottom of the mask to the sleeve can be, for example, 7.5 to 10 cm. a length of the mask (for example in FIG. 2) from one side to the other (e.g., the left side in FIG. 2. To the right side in FIG. 2.) can be 10 cm to 14 cm. In FIG. 16, a height (vertical in FIG. 16) of the foam pad 1503 can be 2.54 cm and the width can be 2 cm. The wire 1600 can be for example 20-22 gauge wire, and the wire coating can be, for example 02-0.04 inch diameter, etc. The portholes 1700 in FIG. 17 can be for example 2.54 cm in diameter. In FIG. 20., the mask 2001 can be 10 cm in height (from the bottom of the mask 2001 to the portion of the mask 2001 abutting the sleeve), the width (e.g., left side to right side in FIG. 20) of the bottom of the mask 2001 can be 10 cm to 12.5 cm, and the length from one pad on the mask 2001 to the other pad on the mask 2001 can be 18 cm (in other words the mask 2001 is ovular shaped). In FIG. 21, the diameter of the sleeve can be for example 10 cm to 12.5 cm (to accommodate the laryngeal mask airway (which is larger than an endotracheal tube).

Figure 26:
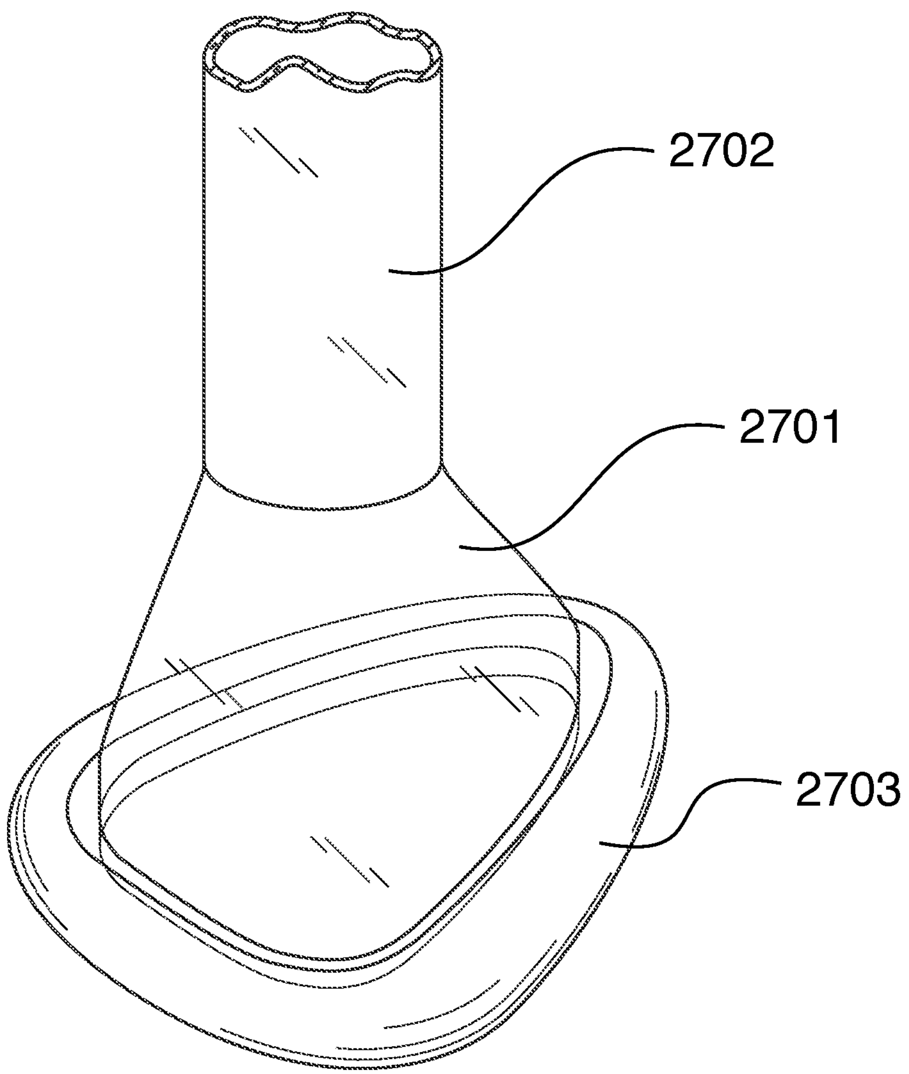
FIG. 26 is a drawing showing a further embodiment of a sanitary extubation cover using an air cushion, according to an embodiment.

Note that the shapes and dimensions described and illustrated herein are one FIG. 26 is a drawing showing a further embodiment of a sanitary extubation cover using an air cushion, according to an embodiment.

In a further embodiment, an air cushion can be used at the bottom of the sanitary extubation cover in order to contact the patient's face. This can provide an airtight seal which is comfortable for the user.

FIG. 26 is a drawing showing a side view of the further embodiment of the sanitary extubation cover using an air cushion, according to an embodiment;

A sleeve 2702 can be the same as any sleeve described herein. A mask 2701 can be the same as any mask described herein. The sleeve 2702 is connected (or attached or integrally a part of) to the mask 2701 which is connected (or attached or integrally a part of) an air cushion 2703. All parts (sleeve 2702, mask 2701, and air cushion 2703) are connected (or sealed or integrated) so that air cannot leak out through any connection. The air cushion 2703 is filled with air and can be made out of any airtight, inflatable material (e.g., rubber, etc.) The air cushion 2703 would typically come already filled with air. The air cushion could be inflated using a syringe to insert more air inside it. The air cushion 2702 is placed firmly against the patient's face so that the patient is comfortable. The air cushion 2702 would not let air escape between the seal of the air cushion and the patient's face (e.g., an airtight seal is made with the air cushion and the patient's face).

Figure 27:
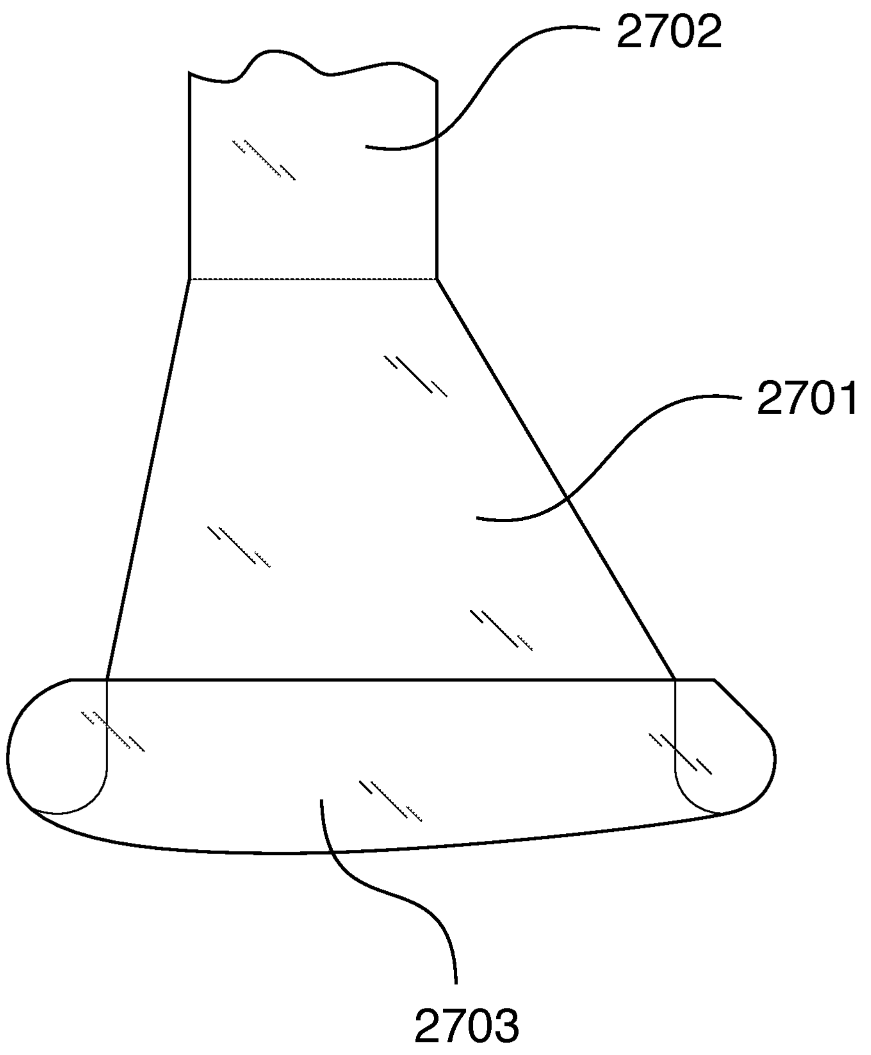
FIG. 27 is a drawing showing a side view of the further embodiment of the sanitary extubation cover using an air cushion, according to an embodiment.

FIG. 27 is a drawing showing a side view of the further embodiment of the sanitary extubation cover using an air cushion, according to an embodiment.

Figure 28:
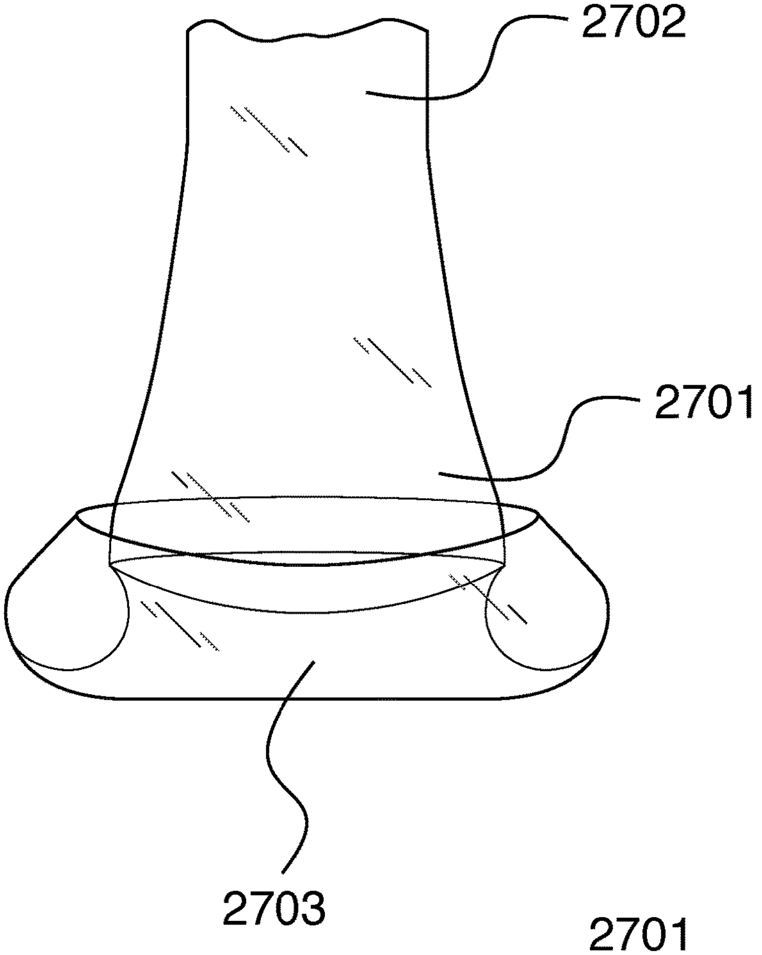
FIG. 28. is a drawing showing a front view of the further embodiment of the sanitary extubation cover using an air cushion, according to an embodiment.
Figure 29:
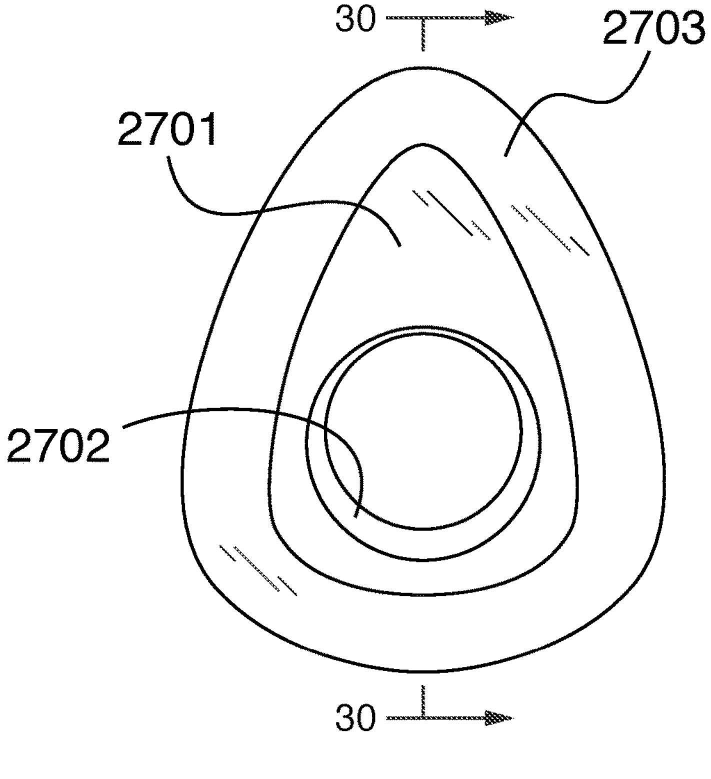
FIG. 29 is a drawing showing a top view of the further embodiment of the sanitary extubation cover using an air cushion, according to an embodiment.
Figure 30:
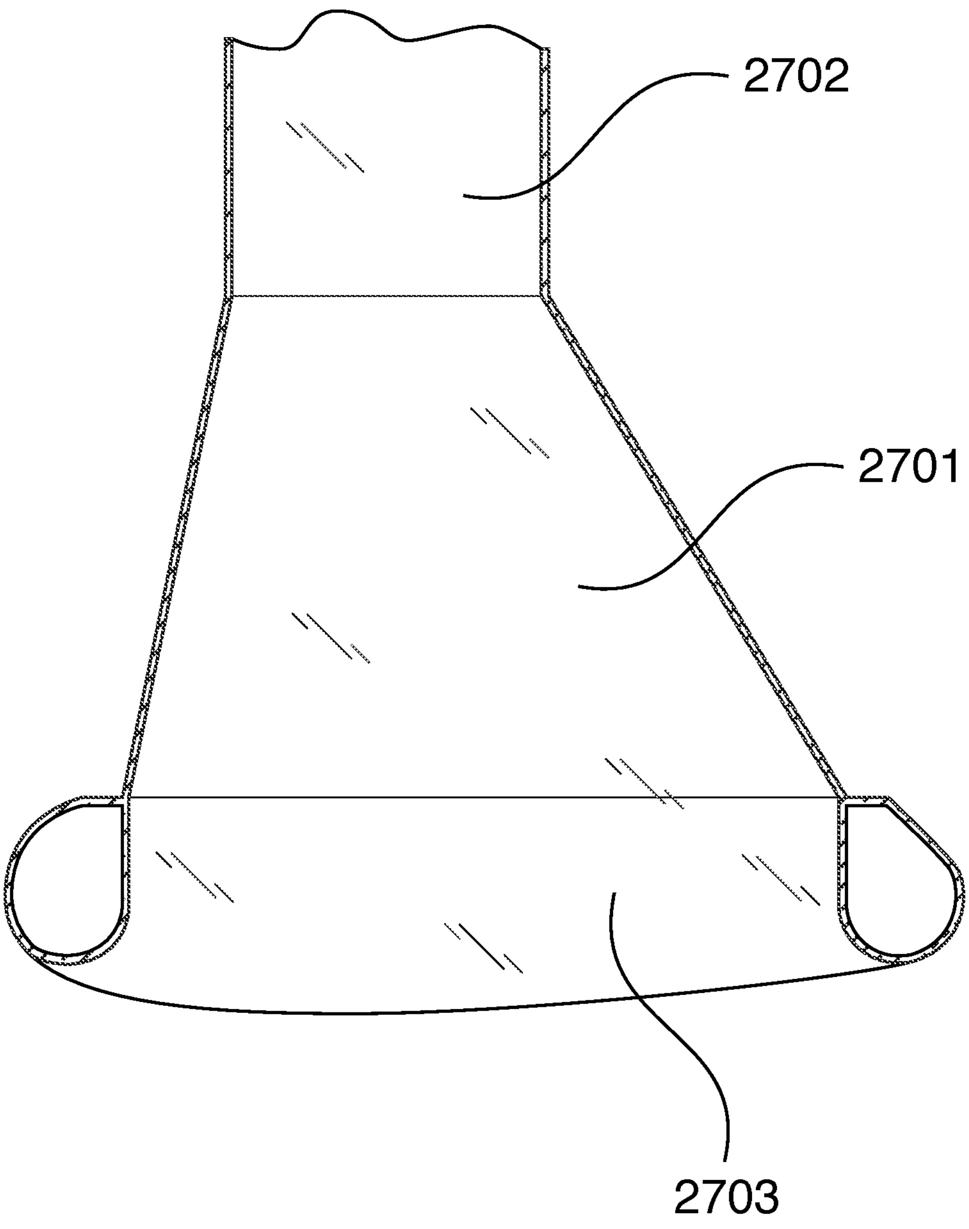
FIG. 30 is a drawing showing a cross section of the sanitary extubation cover from the view shown in FIG. 29, according to an embodiment.
Figure 31:
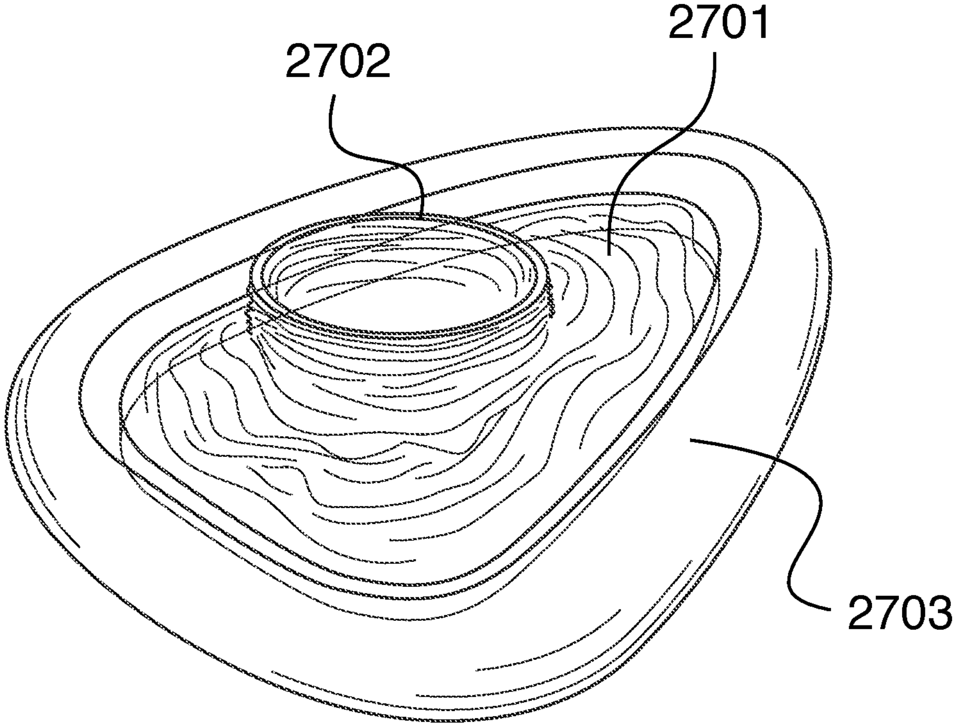
FIG. 31 is a drawing showing a compressed sanitary extubation cover, according to an embodiment.

FIG. 28. is a drawing showing a front view of the further embodiment of the sanitary extubation cover using an air cushion, according to an embodiment;

FIG. 29 is a drawing showing a top view of the further embodiment of the sanitary extubation cover using an air cushion, according to an embodiment;

FIG. 30 is a drawing showing a cross section of the sanitary extubation cover from the view shown in FIG. 29, according to an embodiment; and FIG. 31 is a drawing showing a compressed sanitary extubation cover, according to an embodiment.

In FIG. 26, the sanitary extubation cover using an air cushion is extended, however the sanitary extubation cover using an air cushion can be pushed into a compressed state as shown in FIG. 31.

Note that the sanitary extubating cover as shown in FIGS. 26-31 can be combined/used with any feature/method (including any materials) described herein.

In a further embodiment, in place of the air cushion, a solid silicone base can be used (not inflatable). The silicon base can be entirely made out of any medical grade silicone. The silicone base would typically be soft and malleable and would form fit to the patient's face while remaining comfortable to the patient. Note that FIGS. 26, 29, 31 can also depict the solid silicone base. Note that FIGS. 27, 28 and 30 would not be used to illustrate the solid silicone base. The solid silicone base would be used with any of the other embodiments herein and would replace the base 106 (or air cushion) and is integrally attached/connected to the rest of the mask.

Figure 32:
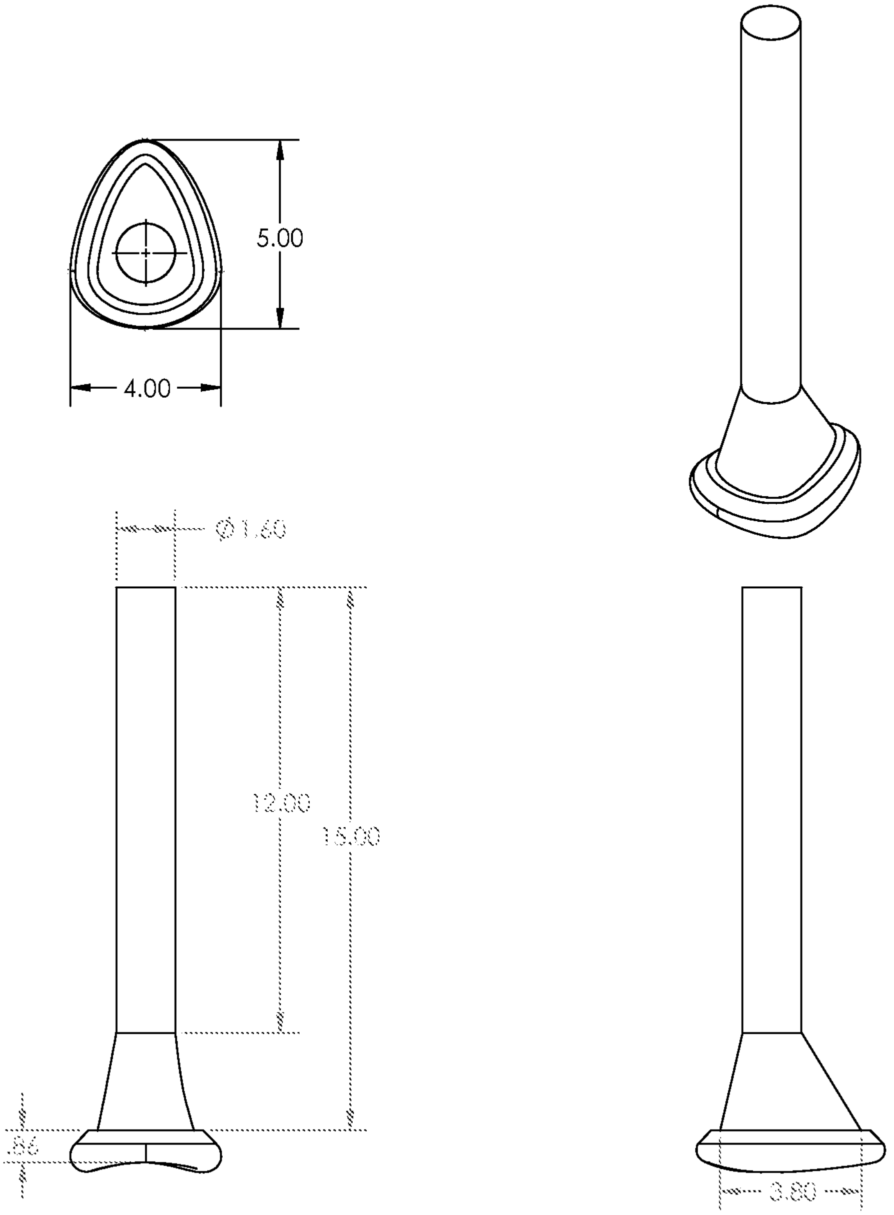
FIG. 32 illustrates a sample set of dimensions for use with the silicone base embodiment.

FIG. 32 illustrates a sample set of dimensions for use with the silicone base embodiment. It is noted that these dimensions are merely one example and other such sets of measurements could be used as well. The measurements shown are in inches.

Figure 33:
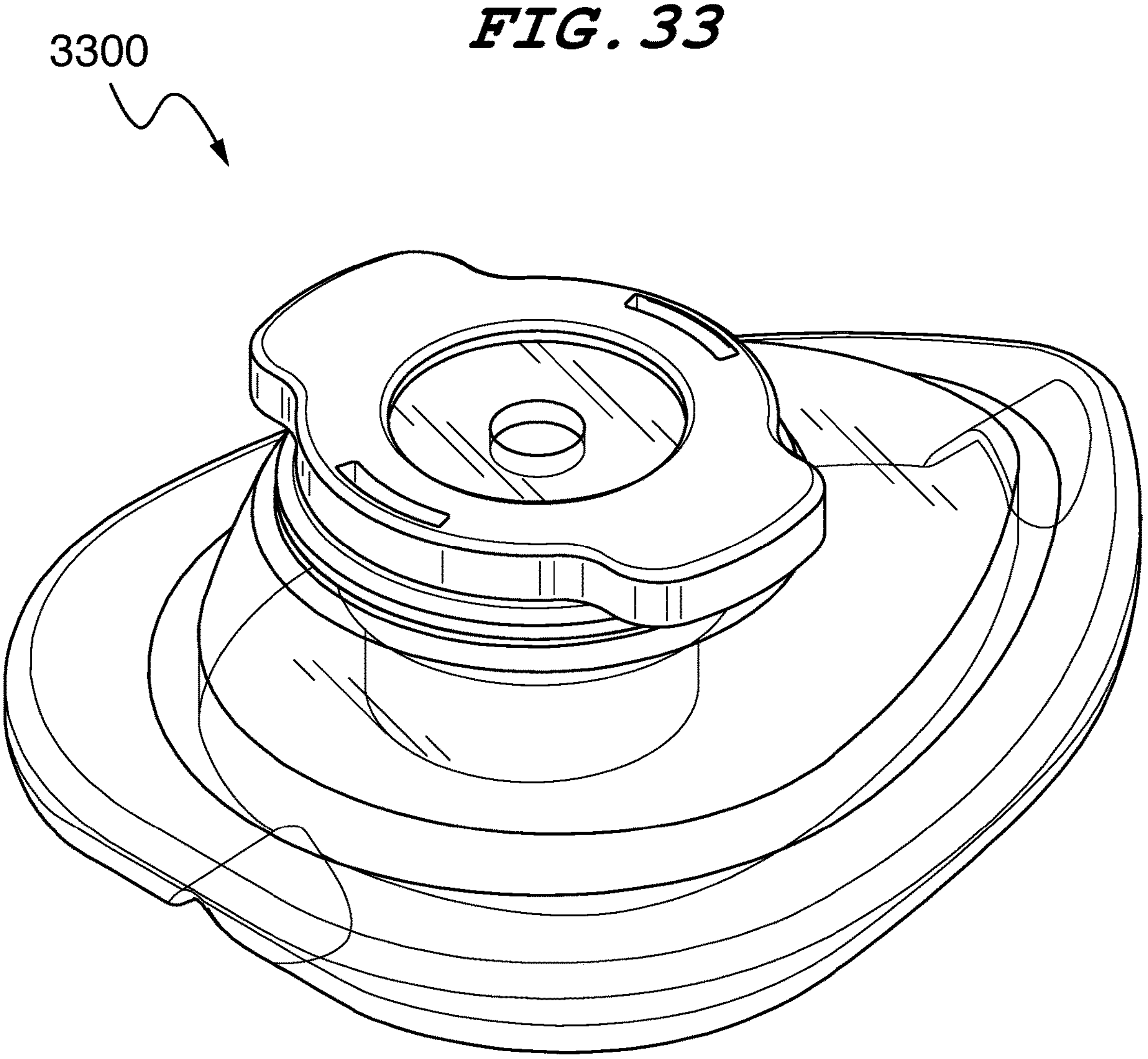
FIG. 33 illustrates a capped sanitary extubation cover, according to an embodiment.

FIG. 33 illustrates a capped sanitary extubation cover, according to an embodiment.

The capped sanitary extubation cover operates in the same manner as any of the other embodiments described above.

Figure 34:
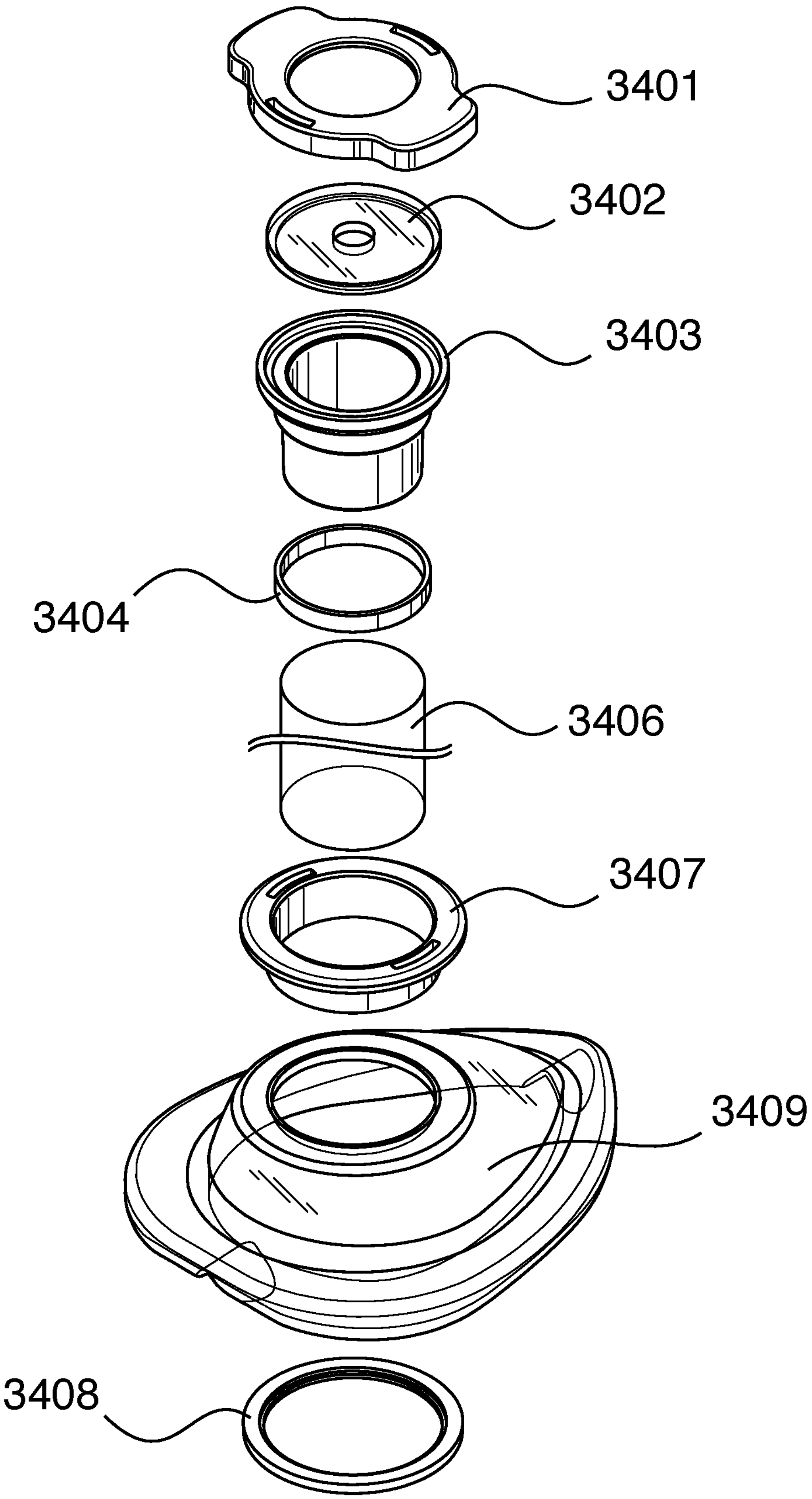
FIG. 34 illustrates the assembly of parts of the capped sanitary extubation cover, according to an embodiment.

FIG. 34 illustrates the assembly of parts of the capped sanitary extubation cover, according to an embodiment.

A cap 3401, disc 3402, cylinder 3403, top ring 3404, sleeve 3406, connector 3407, mask 3409 and bottom ring 3408 all connect to each other using snap/friction fits. While an adhesive (e.g., glue) can be used to attach any combination of parts, this is not required and is optional, as all of the parts shown are configured in size to snap and fit together.

Figure 35:
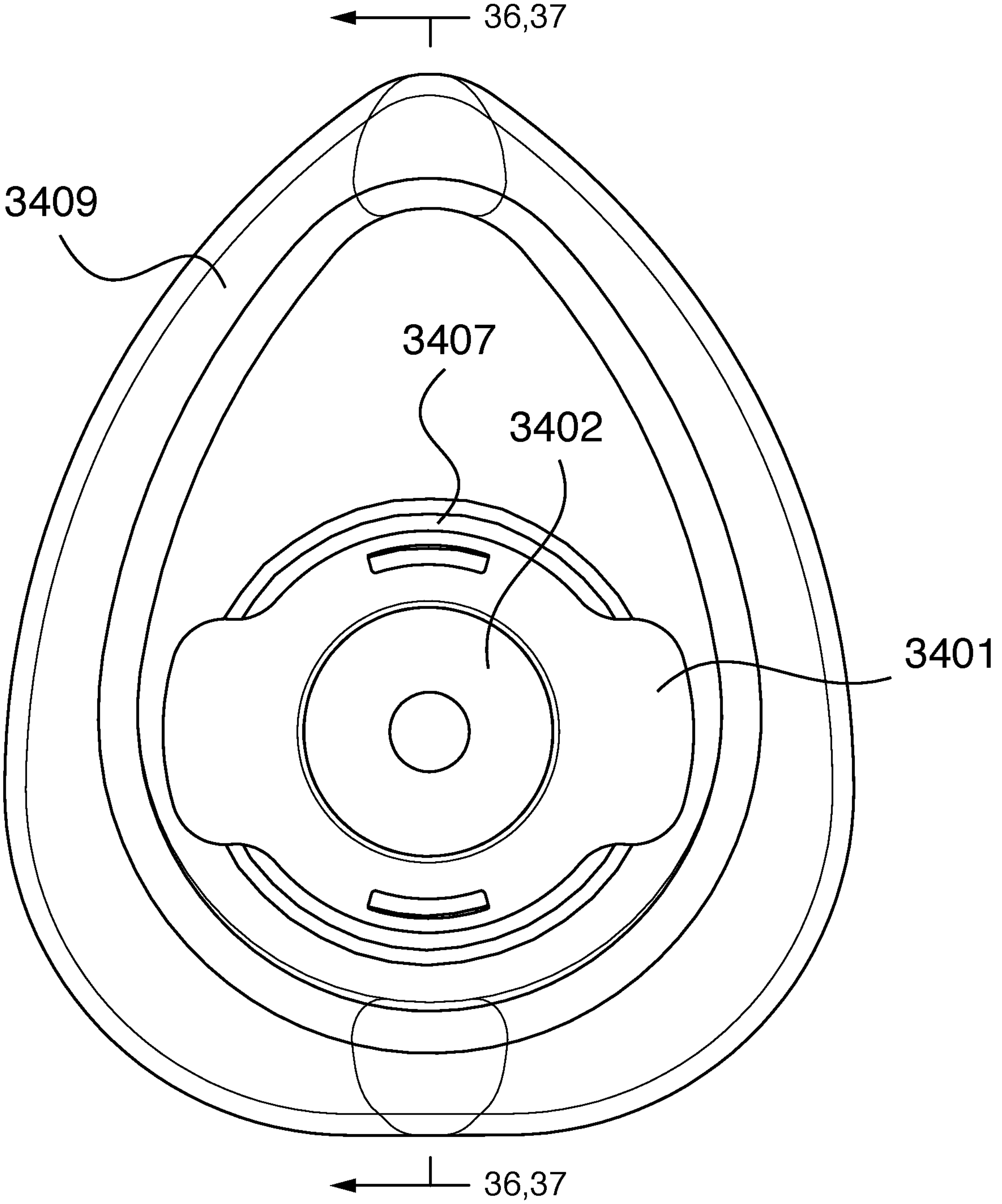
FIG. 35 illustrates a top view of the sanitary extubation cover, according to an embodiment.

FIG. 35 illustrates a top view of the sanitary extubation cover, according to an embodiment.

Note how all of the parts neatly fit together and the cap fits over the mask as shown.

Figure 36:
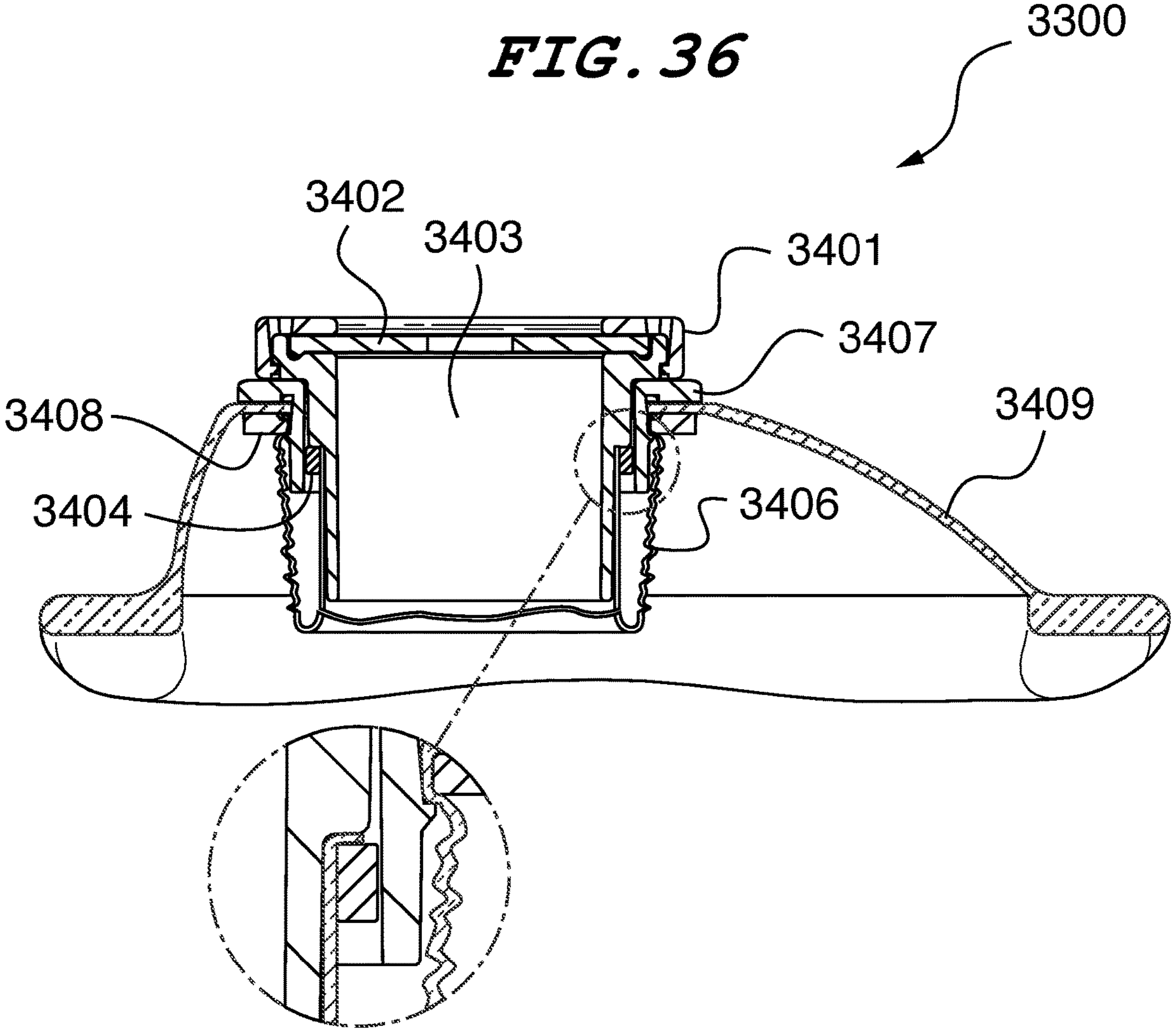
FIG. 36 illustrates a cross section of the sanitary extubation cover from the view shown in FIG. 35, according to an embodiment.

FIG. 36 illustrates a cross section of the sanitary extubation cover from the view shown in FIG. 35, according to an embodiment.

Note how the bottom ring 3408 snaps over (onto) the connector 3407 while the sleeve 3406 is folded back over the connector 3407 so that the sleeve is hermetically sealed to the connector 3407 (and hence the mask 3409. The friction fit between the bottom ring 3408 and the connector 3407 also seals (connects) the mask 3409 as well.

Figure 37:
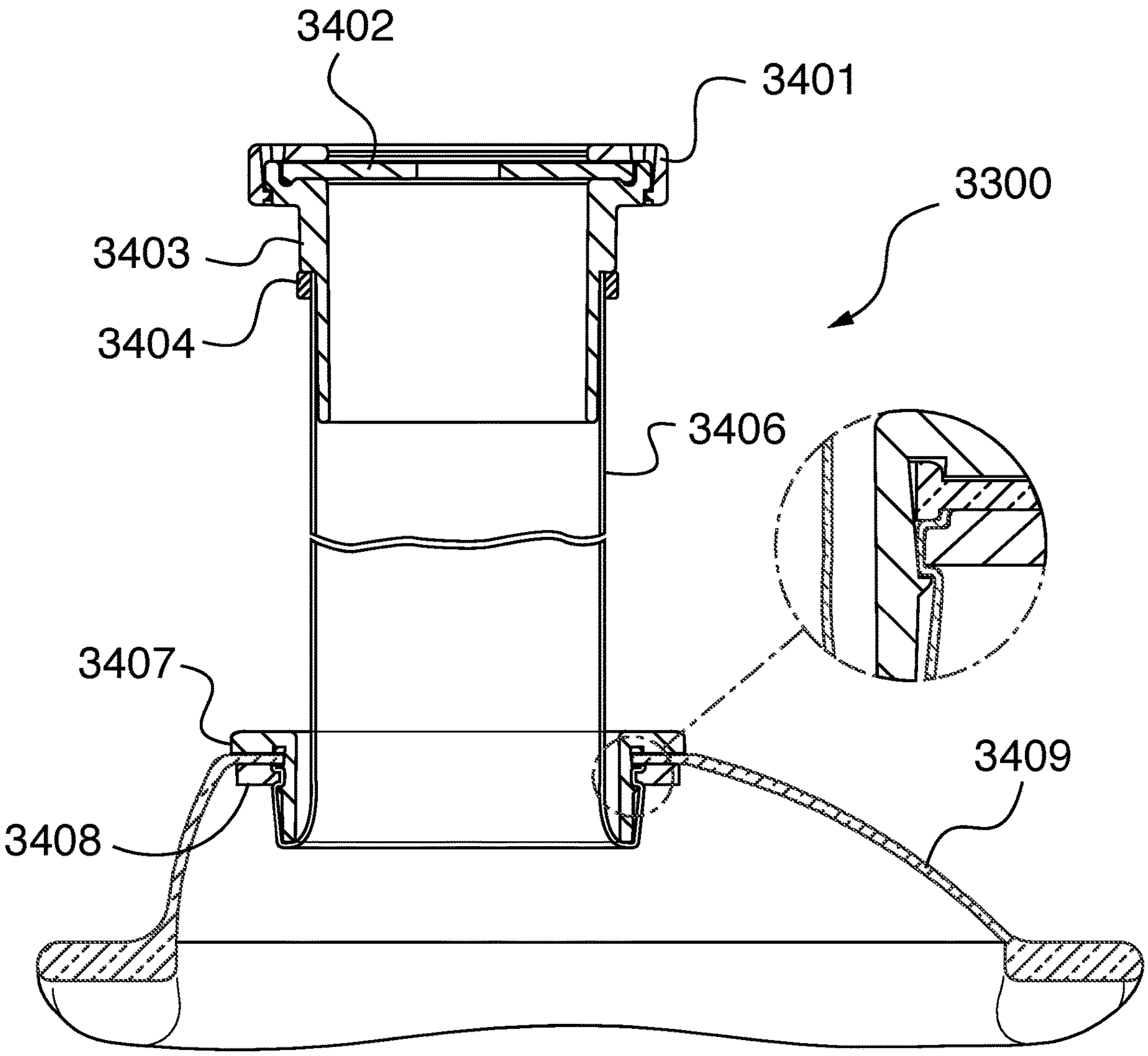
FIG. 37 illustrates a cross section of the sanitary extubation cover from the view shown in FIG. 35, according to an embodiment.

FIG. 37 illustrates a cross section of the sanitary extubation cover from the view shown in FIG. 35 in an extended position, according to an embodiment.

Note how the top ring 3404 snaps over the cylinder 3403 thereby hermetically attaching the sleeve 3406 to the cylinder 3403. Note that the sleeve 3406 is hermetically connected throughout all of the parts to the mask so that no air an escape from the patient's mouth (once the mask is placed against the patient's face) unless it goes out through the top of the cap 3401.

Figure 38:
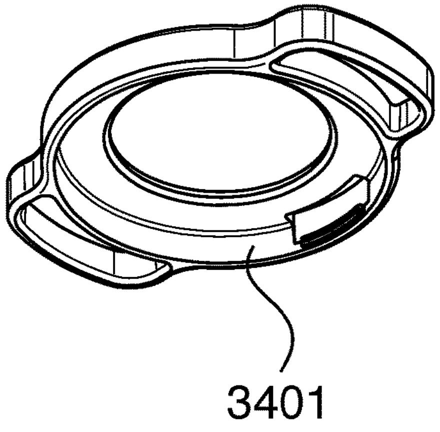
FIG. 38 illustrates the cap of the sanitary extubation cover, according to an embodiment.

FIG. 38 illustrates the cap of the sanitary extubation cover, according to an embodiment.

The cap 3401 is configured to fit over the disc 3402 and the top of the cylinder 3404. The cap can snap fit over cylinder 3404. To unfold sleeve 3406 into the extended position, the user simply needs to lift out the cap 3401.

Figure 39:
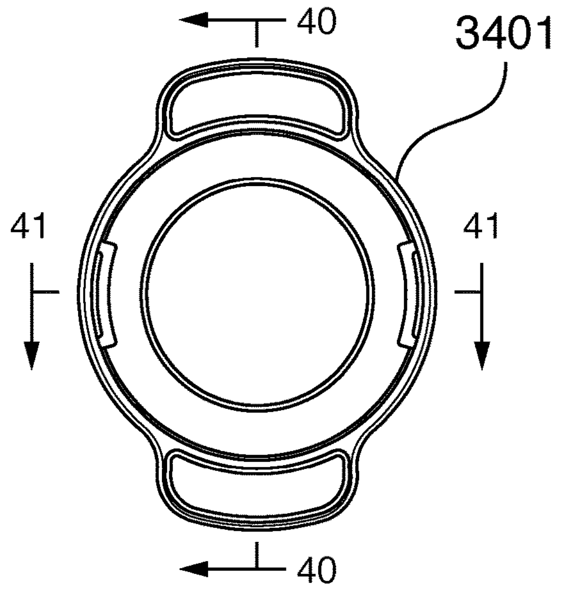
FIG. 39 illustrates a bottom of view of the cap, according to an embodiment.
Figure 40:
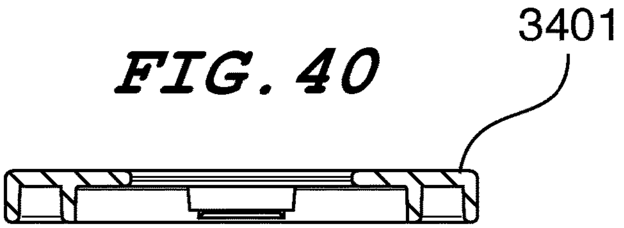
FIG. 40. illustrates a cross section of the cap from the view shown in FIG. 39, according to an embodiment.
Figure 41:
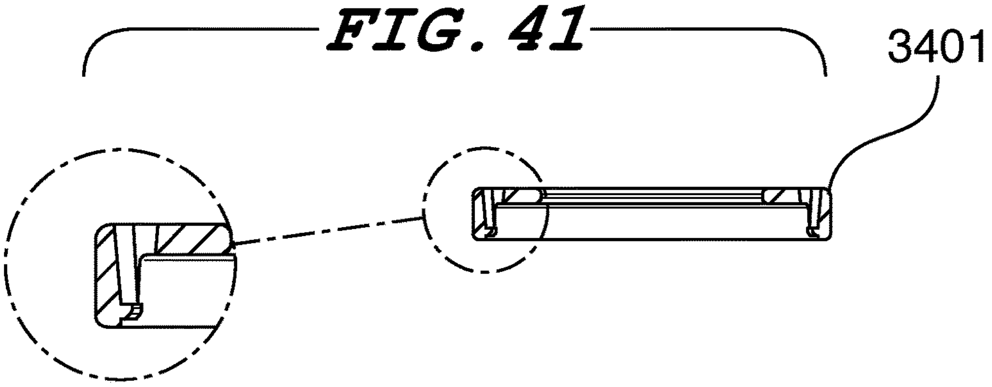
FIG. 41 illustrates a cross section of the cap from the view shown in FIG. 39, according to an embodiment.

FIG. 39 illustrates a bottom of view of the cap, according to an embodiment. FIG. 40. illustrates a cross section of the cap from the view shown in FIG. 39, according to an embodiment. FIG. 41 illustrates a cross section of the cap from the view shown in FIG. 39, according to an embodiment.

Figure 42:
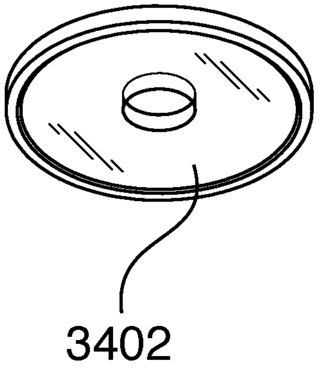
FIG. 42 illustrates a view of the disc, according to an embodiment.
Figure 43:
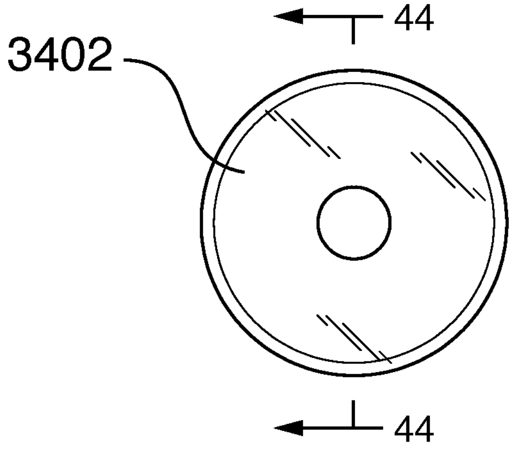
FIG. 43 illustrates a top view of the disc, according to an embodiment.
Figure 44:
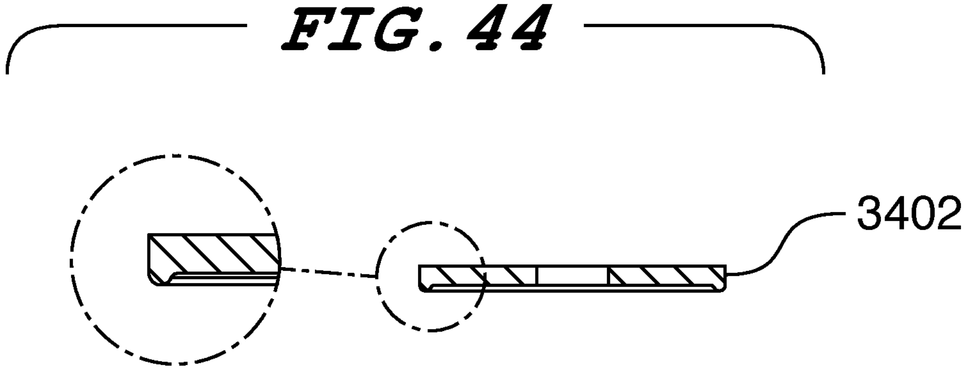
FIG. 44 illustrates a cross section of the disc from the view shown in FIG. 43, according to an embodiment.

FIG. 42 illustrates a view of the disc, according to an embodiment. A hole in the center of the disc 3402 can be used to receive and guide the endotracheal tube. FIG. 43 illustrates a top view of the disc, according to an embodiment. FIG. 44 illustrates a cross section of the disc from the view shown in FIG. 43, according to an embodiment.

Figure 45:
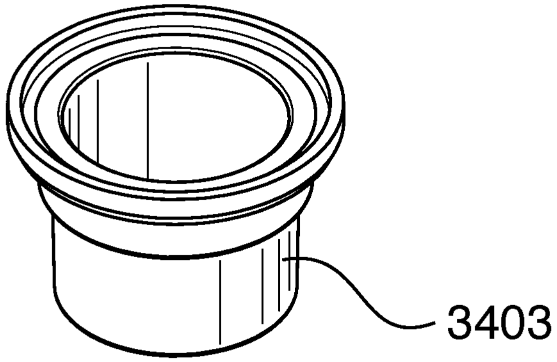
FIG. 45 illustrates a cylinder, according to an embodiment.
Figure 46:
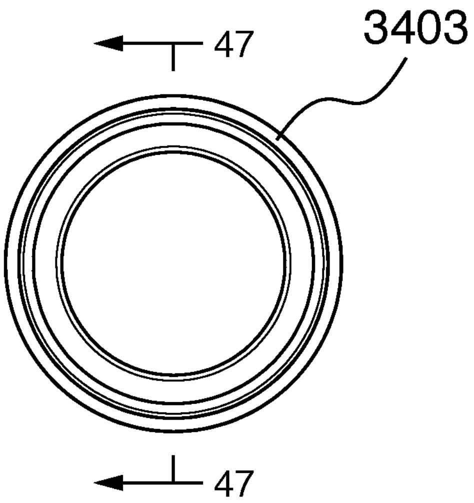
FIG. 46 illustrates a top view of the cylinder, according to an embodiment.
Figure 47:
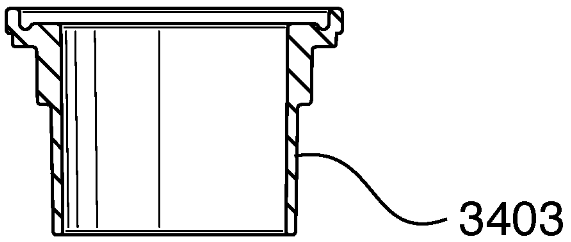
FIG. 47. Illustrates a cross section view of the cylinder from the view shown in FIG. 46, according to an embodiment.

FIG. 45 illustrates a cylinder, according to an embodiment. The cylinder is what the mask and the top part of the sleeve can be attached to hermitically. FIG. 46 illustrates a top view of the cylinder, according to an embodiment. FIG. 47. Illustrates a cross section view of the cylinder from the view shown in FIG. 46, according to an embodiment. The top ring 3404 friction fits tightly over the bottom of the cylinder 3403 thus sealing the top portion of the sleeve 3406 onto the cylinder 3403.

Figure 48:
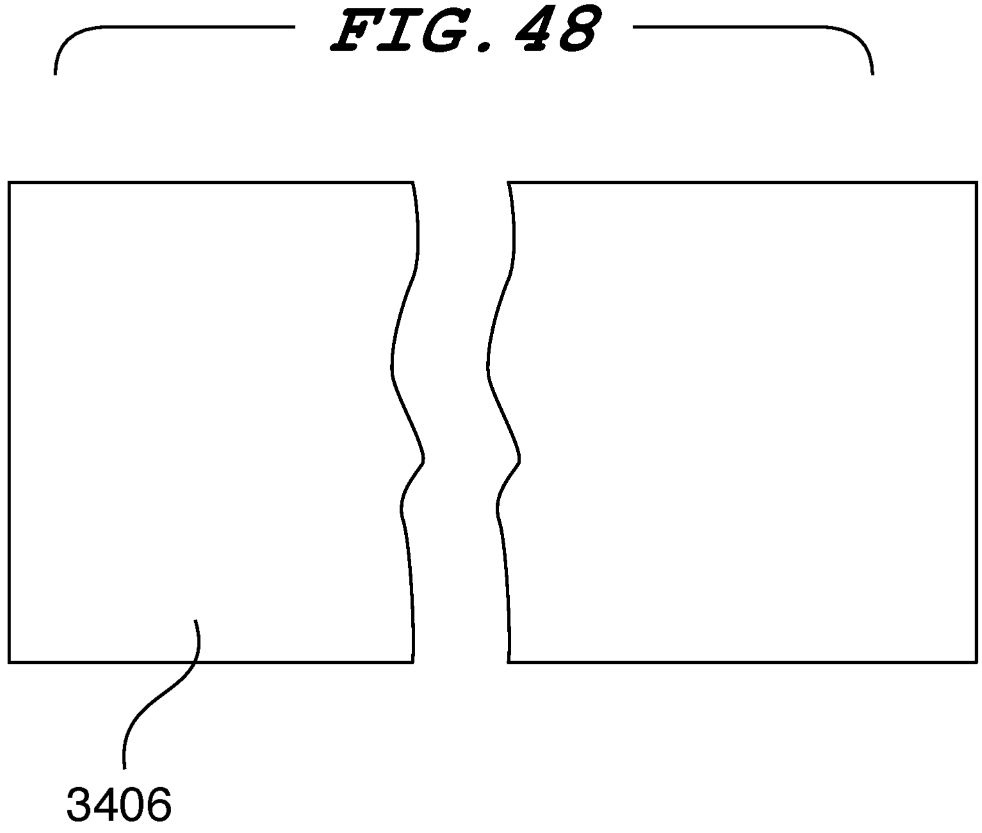
FIG. 48 illustrates a front view of the sleeve in an extended position, according to an embodiment.

FIG. 48 illustrates a front view of the sleeve in an extended position, according to an embodiment. The sleeve can be made out of any material described herein, such as a very thin plastic that can fold and unfold. The sleeve is cylindrical with a hollow center so that air can pass through the sleeve (as described and shown herein).

Figure 49:
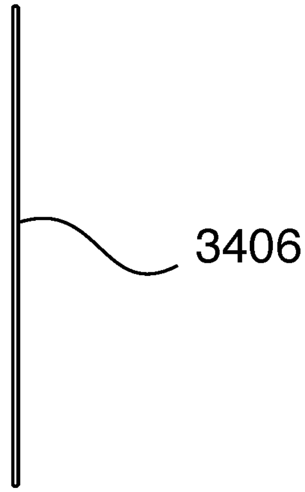
FIG. 49 illustrates a side view of the sleeve in a flat state, according to an embodiment.

FIG. 49 illustrates a side view of the sleeve in a flat state, according to an embodiment. In this view, the sleeve is compressed (folded) although note that air can be pushed through the sleeve 3406 which would cause the sleeve 3406 to expand.

Figure 50:
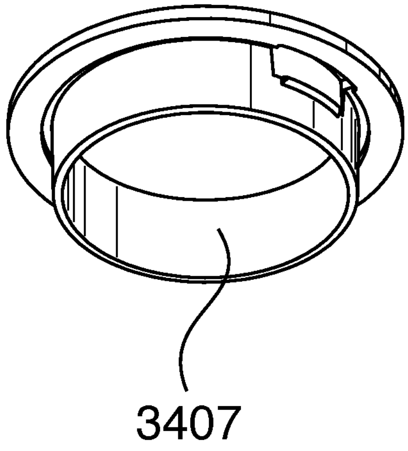
FIG. 50 illustrates a connector, according to an embodiment.
Figure 51:
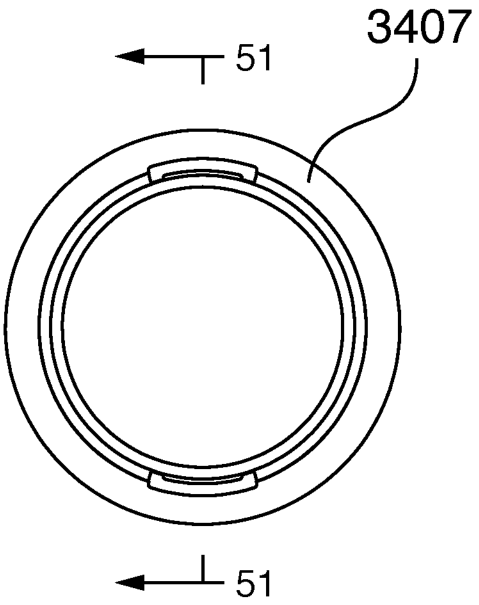
FIG. 51 illustrates a bottom view of the connector, according to an embodiment.
Figure 52:
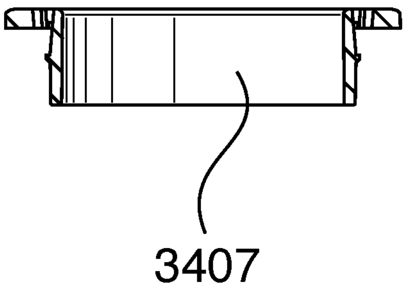
FIG. 52 illustrates a cross section view of the connector from the view shown in FIG. 51, according to an embodiment.

FIG. 50 illustrates a connector, according to an embodiment. The connector 3407 fits through a hole in the mask 3409 and the lower ring 3408 friction fits (snaps) tightly over the bottom of the connector 3407. The bottom portion of the sleeve 3406 also goes through the hole in the connector 3407 and then folds upwards around the perimeter of the bottom of the connector 3407 upon which the bottom ring 3408 then fits tightly around, thereby sealing the bottom portion of the sleeve 3406 onto the connector 3407. FIG. 51 illustrates a bottom view of the connector, according to an embodiment. FIG. 52 illustrates a cross section view of the connector from the view shown in FIG. 51, according to an embodiment.

Figure 53:
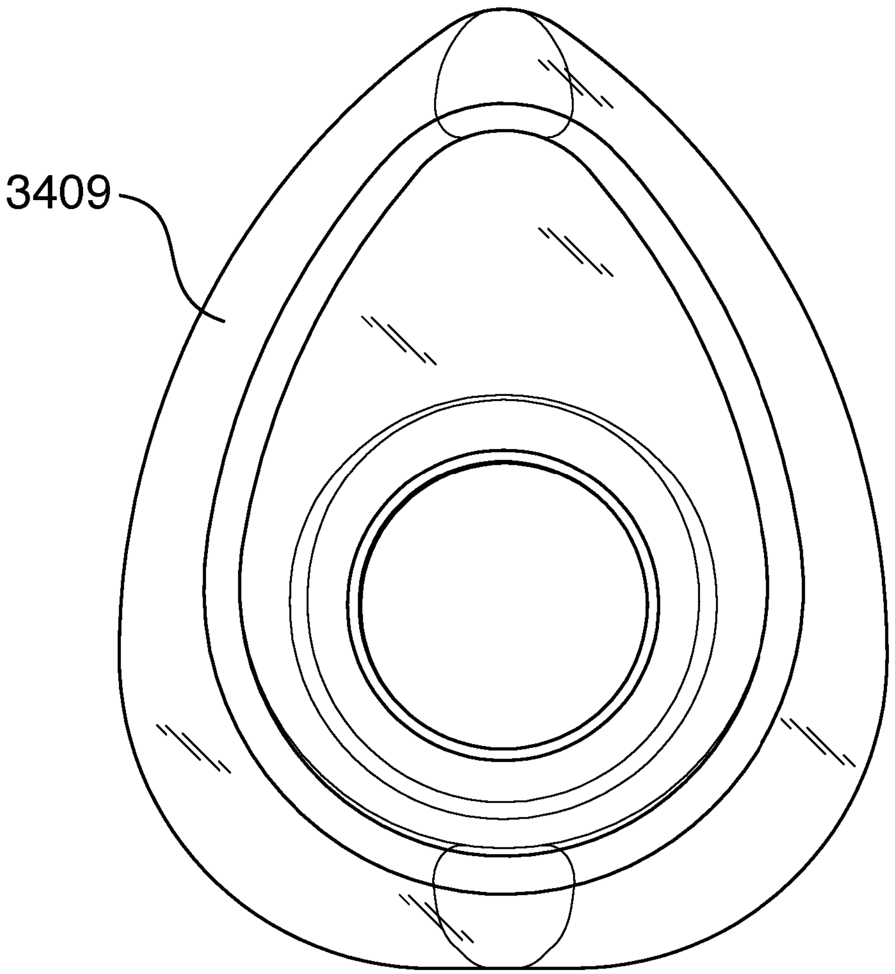
FIG. 53 illustrates a top view of the mask, according to an embodiment.
Figure 54:
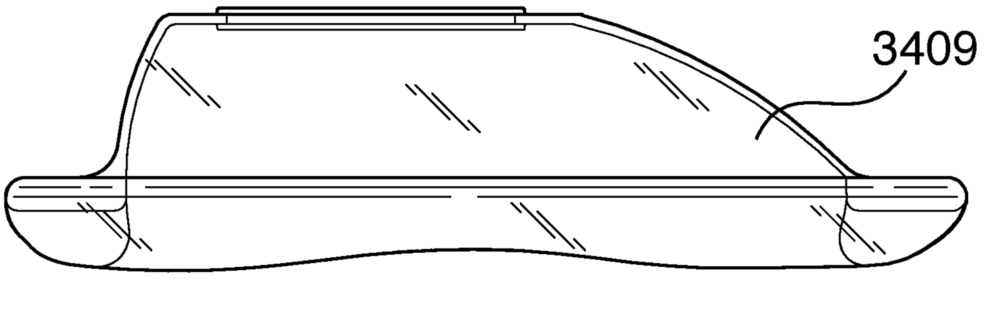
FIG. 54 illustrates a side view of the mask, according to an embodiment.

FIG. 53 illustrates a top view of the mask, according to an embodiment. The mask 3409 can be made of a solid silicone base can be used. The silicon base can be entirely made out of any medical grade silicone. The silicone base would typically be soft and malleable and would form fit to the patient's face while remaining comfortable to the patient. FIG. 54 illustrates a side view of the mask, according to an embodiment.

Figure 55:
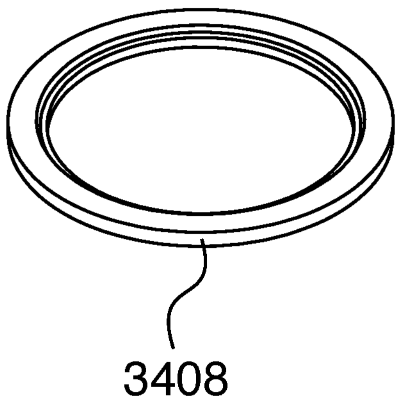
FIG. 55 illustrates a bottom ring, according to an embodiment.
Figure 56:
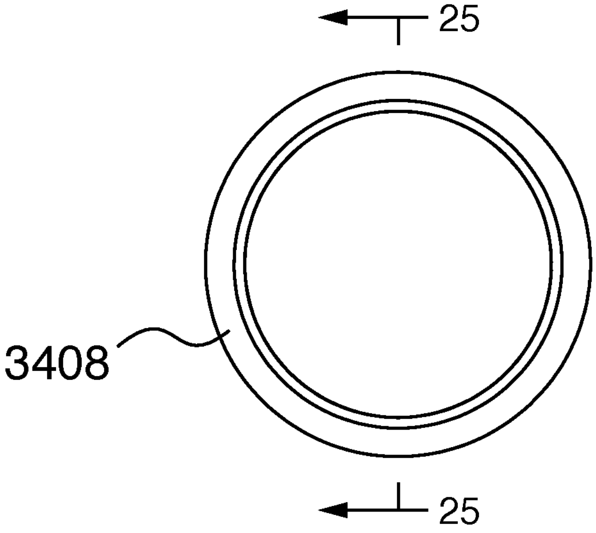
FIG. 56 illustrates a top view of the bottom ring, according to an embodiment.
Figure 57:
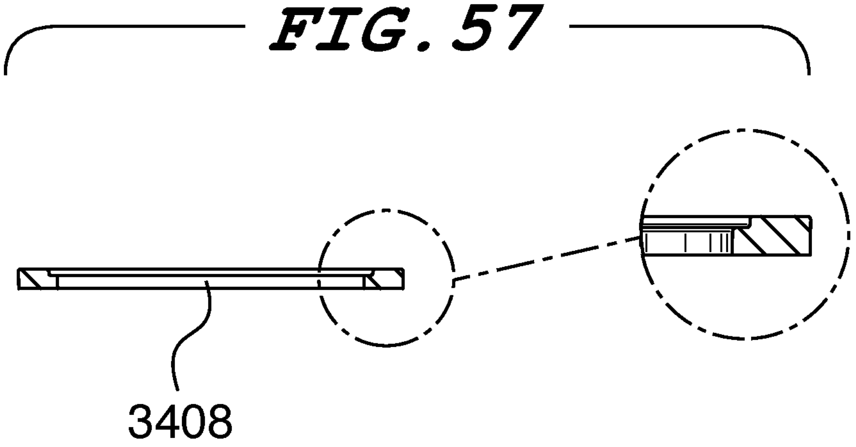
FIG. 57 illustrates a cross section of the bottom ring from the view shown in FIG. 56, according to an embodiment.

FIG. 55 illustrates a bottom ring, according to an embodiment. The bottom ring is configured to fit tightly over the connector 3407. FIG. 56 illustrates a top view of the bottom ring, according to an embodiment. FIG. 57 illustrates a cross section of the bottom ring from the view shown in FIG. 56, according to an embodiment.

Figure 58:
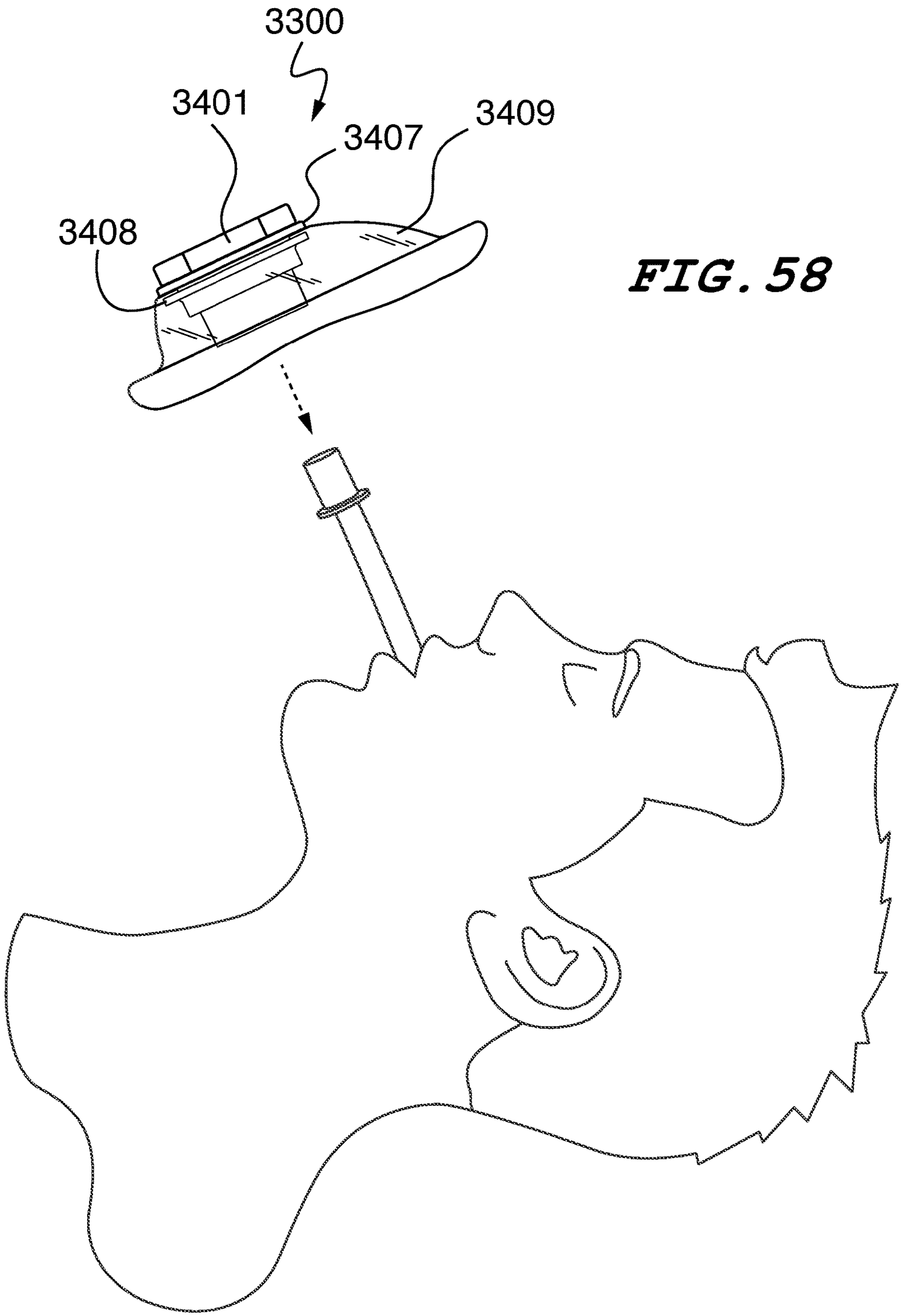
FIG. 58 illustrates how the capped sanitary extubation cover is applied, according to an embodiment.

FIG. 58 illustrates how the capped sanitary extubation cover is applied, according to an embodiment. The capped sanitary extubation cover is placed over the endotracheal tube as shown.

Figure 59:
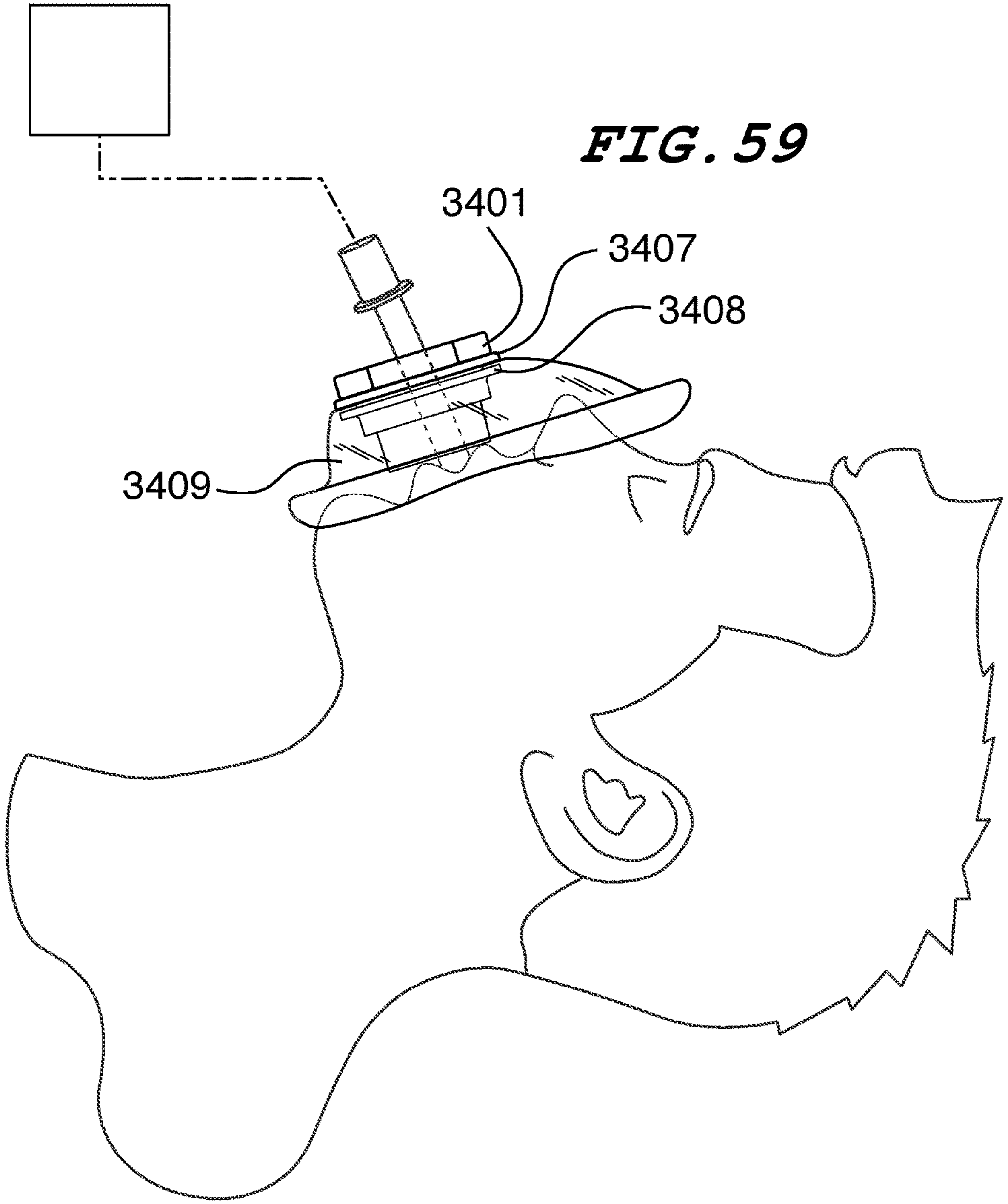
FIG. 59 illustrates the capped sanitary extubation cover applied to a patient's face, according to an embodiment.

FIG. 59 illustrates the capped sanitary extubation cover applied to a patient's face, according to an embodiment.

The mask 3409 of the capped sanitary extubation cover is placed directly against the patient's face as shown. Typically, air form the patient's mouth can only escape through the sanitary extubation cover. The end of the endotracheal tube would be connected to a ventilator (as described herein with regard to the other embodiments).

Figure 60:
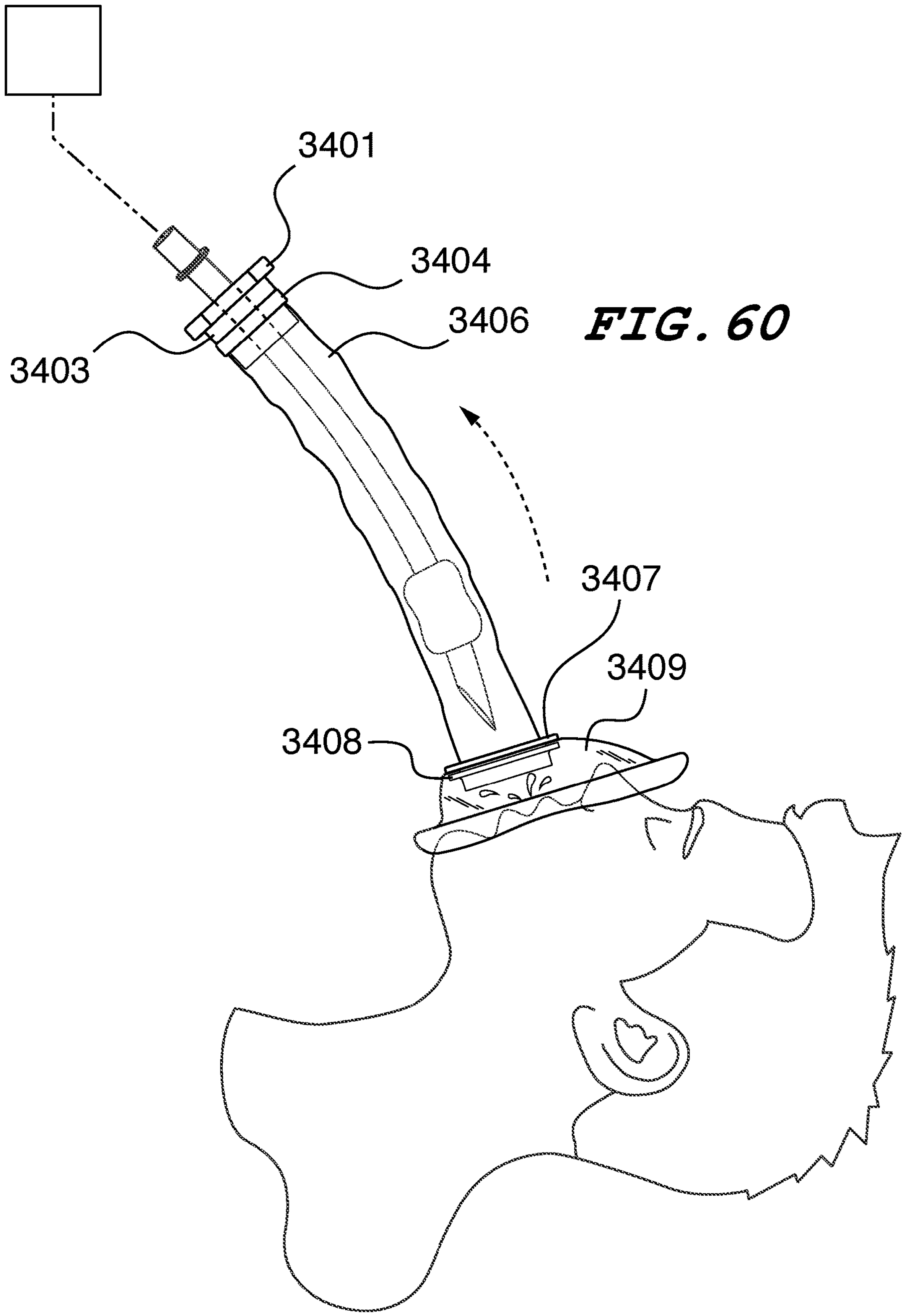
FIG. 60 illustrates the capped sanitary extubation cover with the sleeve extended, according to an embodiment.

FIG. 60 illustrates the capped sanitary extubation cover with the sleeve extended, according to an embodiment.

The sleeve 3406 is extended (in the same manner as the other embodiments described herein) as the endotracheal tube is removed from the patient's mouth. If the patient coughs the debris from the cough is captured inside the sleeve 3406 and cannot escape the sanitary extubation cover.

Figure 61:
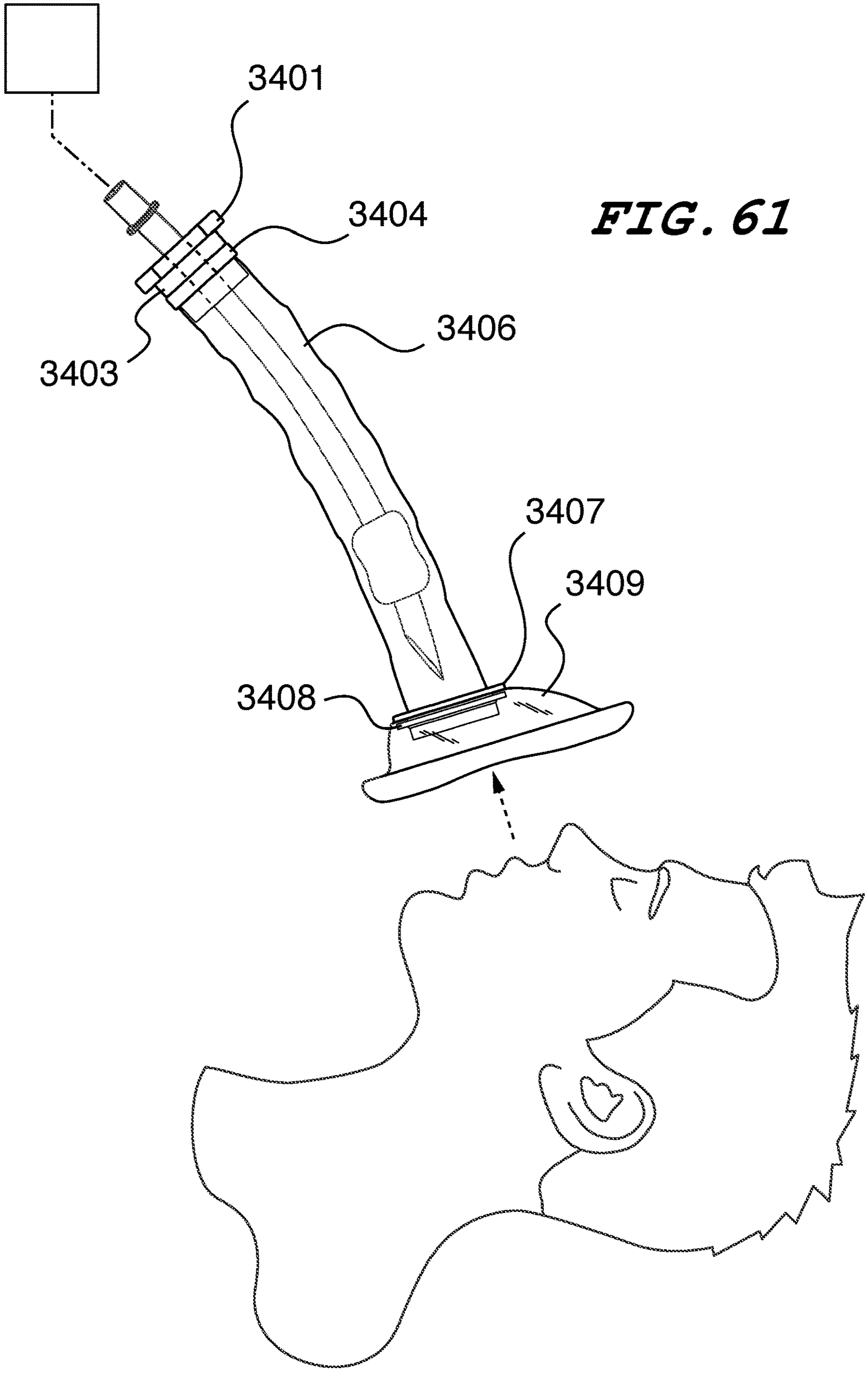
FIG. 61 illustrates removal of the capped sanitary extubation cover, according to an embodiment.

FIG. 61 illustrates removal of the capped sanitary exubation cover, according to an embodiment.

The sanitary extubation cover is then removed from the patient's face with the debris inside and safely discarded.

Note that all of the parts described herein can be made from any suitable materials, including hard plastic.

Note that the shapes and dimensions described and illustrated herein are one embodiment of the inventive concept, and it can be appreciated that the invention can be constructed using structures of different dimensions, sizes, and/or shapes. Each individual part, or combination of parts, can be made using different shapes than what is described/illustrated herein. Changes in shape, structure, size, etc. can be major (different shapes altogether than what is illustrated/described herein) or minor, etc. Any length or size mentioned herein is merely an example, and it can be appreciated that many different sizes can be utilized as well while still applying the inventive concepts described herein. In addition, any materials mentioned herein are also exemplary, and it can be appreciated that any part described herein can be made out of any suitable material (including any material described herein or not described herein). If a material is not set forth herein for a part described herein, it can be appreciated that such part can be constructed using any suitable material or using any material mentioned herein. All features described herein can be combined with each other in any combination.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. An apparatus, comprising:

a mask configured to fit over a person's face;

a connector on the mask;

a hollow cylinder configured to be inserted into the connector;

an expandable hollow sleeve in between the cylinder and the mask, the expandable hollow sleeve hermetically connected to both the connector and the cylinder;

a ring that hermetically seals the expandable sleeve to the connector and also seals the connector to the mask; and a cap configured to snap fit over the cylinder and connected to the cylinder, wherein the expandable hollow sleeve is configured to expand when the cap and cylinder are lifted away from the mask.

2. The apparatus as recited in claim 1, wherein the mask is made out of silicone.

* * * * *